(12) United States Patent
Rodriguez et al.

(10) Patent No.: US 6,781,044 B2
(45) Date of Patent: *Aug. 24, 2004

(54) PLANT SELECTABLE MARKER AND PLANT TRANSFORMATION METHOD

(75) Inventors: Raymond L. Rodriguez, Davis, CA (US); Ning Huang, Davis, CA (US)

(73) Assignee: Ventria Bioscience, Sacramento, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/932,328

(22) Filed: Aug. 17, 2001

(65) Prior Publication Data

US 2003/0028925 A1 Feb. 6, 2003

Related U.S. Application Data

(63) Continuation-in-part of application No. 09/344,438, filed on Jun. 25, 1999, now Pat. No. 6,284,956.
(60) Provisional application No. 60/090,896, filed on Jun. 25, 1998.

(51) Int. Cl.$^7$ .................. C12N 15/82; C12N 15/56; C12N 15/54; A01H 5/00; A01H 5/10
(52) U.S. Cl. .............. 800/320.2; 800/287; 800/300; 800/278; 435/193; 435/204; 435/209; 435/430.1; 435/468
(58) Field of Search .................. 800/278, 287, 800/300, 320.2; 435/193, 204, 209, 430.1, 468

(56) References Cited

U.S. PATENT DOCUMENTS

| | | | |
|---|---|---|---|
| 5,420,034 A | 5/1995 | Kridl et al. | |
| 6,284,956 B1 * | 9/2001 | Rodriguez et al. | 800/320.2 |
| 6,288,303 B1 * | 9/2001 | Rodriguez | 800/287 |

FOREIGN PATENT DOCUMENTS

WO  WO 93/05164  3/1993

OTHER PUBLICATIONS

Hadi et al. Plant Cell Reports 15: 500–505, 1996.
Li et al. Plant Cell Reports 12: 250–255, 1993.
Simmons et al. Plant Molecular Biology 18:33–45, 1992.
Kim et al. Plant Molecular Biology 24:105–117, 1994.
Mol. Biol. of the Cell, Garland Publishing, Inc., New York, NY pp. 551–612, 1989.
Chan et al. Plant Mol. Biol. 22: 491–506, 1993.
Chen, L., et al., "Expression and inheritance of multiple transgenes in rice plants" Nature Biotechnology 16:1060–1064 (1988).
Michelmore, R., "Big news for plant transformation" Nature Biotechnology 14:1653–1654 (1996).
Shimamoto, K., et al., "Fertile transgenic rice plants regenerated from transformed protoplasts" Nature 338:274–276 (1989).
Shizuya, H., et al., "Cloning and stable maintenance of 300–kilobase–pair fragments of human DNA in *Escherichia coli* using an F–factor–based vector" Proc. Natl. Acad. Sci. USA 89:8794–8797 (1992).
Yang, D., et al., "Construction of a bacterial artificial chromosome (BAC) library and identification of overlapping BAC clones with chromosome 4–specific RFLP markers in rice" Theor Appl Gene 95:1147–1154 (1997).

* cited by examiner

*Primary Examiner*—David T. Fox
(74) *Attorney, Agent, or Firm*—Perkins Coie LLP

(57) ABSTRACT

A plant transformation vector for transforming host plant cells with a chimeric selectable marker gene is disclosed. The gene includes, operatively linked in sequence in a 5' to 3' direction, (i) a DNA promoter sequence from the rice beta-glucanase 9 (gns9) gene; (ii) a selectable marker gene, and (iii) a 3' untranslated terminator region. Also disclosed are a vector pair containing the transformation vector, a method of obtaining transformed monocots whose seeds produce a selected heterologous protein during sed germination, and a plant whose cells are transformed with the chimeric selectable marker gene.

8 Claims, 13 Drawing Sheets pAPI25 pAPI65 pAPI96 pAPI92 p3DG pGFP

37B13

44C24

```
            10        20        30        40        50        60        70
CACCTAAATTGTAAGCGTTAATATTTTGTTAAAATTCGCGTTAAATTTTTGTTAAATCAGCTCATTTTTT
GTGGATTTAACATTCGCAATTATAAAACAATTTTAAGCGCAATTTAAAAACAATTTAGTCGAGTAAAAAA 80        90        100       110       120       130       140
AACCAATAGGCCGAAATCGGCAAAATCCCTTATAAATCAAAAGAATAGACCGAGATAGGGTTGAGTGTTG
TTGGTTATCCGGCTTTAGCCGTTTTAGGGAATATTTAGTTTTCTTATCTGGCTCTATCCCAACTCACAAC 150       160       170       180       190       200       210
TTCCAGTTTGGAACAAGAGTCCACTATTAAAGAACGTGGACTCCAACGTCAAAGGGCGAAAAACCGTCTA
AAGGTCAAACCTTGTTCTCAGGTGATAATTTCTTGCACCTGAGGTTGCAGTTTCCCGCTTTTTGGCAGAT 220       230       240       250       260       270       280
TCAGGGCGATGGCCCACTACGTGAACCATCACCCTAATCAAGTTTTTTGGGGTCGAGGTGCCGTAAAGCA
AGTCCCGCTACCGGGTGATGCACTTGGTAGTGGGATTAGTTCAAAAAACCCCAGCTCCACGGCATTTCGT 290       300       310       320       330       340       350
CTAAATCGGAACCCTAAAGGGAGCCCCCGATTTAGAGCTTGACGGGGAAAGCCGGCGAACGTGGCGAGAA
GATTTAGCCTTGGGATTTCCCTCGGGGGCTAAATCTCGAACTGCCCCTTTCGGCCGCTTGCACCGCTCTT 360       370       380       390       400       410       420
AGGAAGGGAAGAAAGCGAAAGGAGCGGGCGCTAGGGCGCTGGCAAGTGTAGCGGTCACGCTGCGCGTAAC
TCCTTCCCTTCTTTCGCTTTCCTCGCCCGCGATCCCGCGACCGTTCACATCGCCAGTGCGACGCGCATTG 430       440       450       460       470       480       490
CACCACACCCGCCGCGCTTAATGCGCCGCTACAGGGCGCGTCCCATTCGCCATTCAGGCTGCGCAACTGT
GTGGTGTGGGCGGCGCGAATTACGCGGCGATGTCCCGCGCAGGGTAAGCGGTAAGTCCGACGCGTTGACA 500       510       520       530       540       550       560
TGGGAAGGGCGATCGGTGCGGGCCTCTTCGCTATTACGCCAGCTGGCGAAAGGGGATGTGCTGCAAGGC
ACCCTTCCCGCTAGCCACGCCCGGAGAAGCGATAATGCGGTCGACCGCTTTCCCCCTACACGACGTTCCG 570       580       590       600       610       620       630
GATTAAGTTGGGTAACGCCAGGGTTTTCCCAGTCACGACGTTGTAAAACGACGGCCAGTGAATTGTAATA
CTAATTCAACCCATTGCGGTCCCAAAAGGGTCAGTGCTGCAACATTTTGCTGCCGGTCACTTAACATTAT

>_Gns9_Promoter
              |
            640       650       660       670       680       690       700
CGACTCACTATAGGGCGAATTGGAGCTCAACTTTAGTCCATATATTTAGACACTAATTTAGAGTATTAAA
GCTGAGTGATATCCCGCTTAACCTCGAGTTGAAATCAGGTATATAAATCTGTGATTAAATCTCATAATTT 710       720       730       740       750       760       770
TATAAATTACTTACAAAACTAATTCAATAAATGAAAGCTAATTTGCGAGACAAATTTTTTATGTTTAATT
ATATTTAATGAATGTTTTGATTAAGTTATTTACTTTCGATTAAACGCTCTGTTTAAAAAATACAAATTAA
```

FIG. 5A

```
              780       790       800       810       820       830       840
    AATCCATAATTAGAGAATGTTTACTGTAGCATCACATAGACTAATCATGGATTAATTAGGCTCAATAGAT
    TTAGGTATTAATCTCTTACAAATGACATCGTAGTGTATCTGATTAGTACCTAATTAATCCGAGTTATCTA 850       860       870       880       890       900       910
    TCGTCTCGTGAATTAGTCCAAGATTATGGATGGATTTTATTAATAGTCTACGTTTAATATTTATAATTAG
    AGCAGAGCACTTAATCAGGTTCTAATACCTACCTAAAATAATTATCAGATGCAAATTATAAATATTAATC 920       930       940       950       960       970       980
    TGTTCAAACATCCGATGTGATAGGGACTTAAAAAGTTTAGTCCCATCTAAACAGGGCCACAGTCTATGTG
    ACAAGTTTGTAGGCTACACTATCCCTGAATTTTCAAATCAGGGTAGATTTGTCCCGGTGTCAGATACAC 990      1000      1010      1020      1030      1040      1050
    GAGCATGTTCACCGAACACCGATAAATATTGCAAAGCCCAGAATGATTTTGGTCCCACATGCCAGAAACT
    CTCGTACAAGTGGCTTGTGGCTATTTATAACGTTTCGGGTCTTACTAAAACCAGGGTGTACGGTCTTTGA 1060      1070      1080      1090      1100      1110      1120
    ACCACACCCACATTTCGGTTCATTTTCAGCTCAGGAAAATCGTCCAACAATTTCAGCTCAGGAAATTAAA
    TGGTGTGGGTGTAAAGCCAAGTAAAAGTCGAGTCCTTTTAGCAGGTTGTTAAAGTCGAGTCCTTTAATTT 1130      1140      1150      1160      1170      1180      1190
    TCGTCCGAGAAAGGAACAAGTTTGGAGCCGTTGGGATGAGAGCAATTAGGTCACGCTTAACTACAAGTAC
    AGCAGGCTCTTTCCTTGTTCAAACCTCGGCAACCCTACTCTCGTTAATCCAGTGCGAATTGATGTTCATG 1200      1210      1220      1230      1240      1250      1260
    AGTCTCATTCATCGACATTGATTAGCCAGCAACTAACCACTTAACCCCGAGCCAGCCCAAGCGCTCCGTA
    TCAGAGTAAGTAGCTGTAACTAATCGGTCGTTGATTGGTGAATTGGGGCTCGGTCGGGTTCGCGAGGCAT 1270      1280      1290      1300      1310      1320      1330
    CGTTCGTTGGGCCCCGCCGCGCAGGCGGAGACAACGGTCATCCGGCGCGCCGGTCGCTCTCCCTCGCTC
    GCAAGCAACCCGGGGCGGCGCGTCCGCCTCTGTTGCCAGTAGGCCGCGCGGCCAGCGAGAGGGAGCGAG 1340      1350      1360      1370      1380      1390      1400
    GCACGGCCGCACCACCCACTTCGCCACGAACCCGACGCGAGCGCGACGTGCATCTCCCAACATCCCCGCC
    CGTGCCGGCGTGGTGGGTGAAGCGGTGCTTGGGCTGCGCTCGCGCTGCACGTAGAGGGTTGTAGGGGCGG 1410      1420      1430      1440      1450      1460      1470
    ATTTCCTCCCCACCCAAAACCAACCCGCCCGCGTGCGGCTGGCCCACTTTACAGCGCCTCACCTCCCCCA
    TAAAGGAGGGGTGGGTTTTGGTTGGGCGGGCGCACGCCGACCGGGTGAAATGTCGCGGAGTGGAGGGGGT 1480      1490      1500      1510      1520      1530      1540
    ACCATAAATCCCCGCCCTTTTCCCCCCCTCTCCACCACTCACCACGCTCTCCACTACACGACTCGTCGCC
    TGGTATTTAGGGGCGGGAAAAGGGGGGAGAGGTGGTGAGTGGTGCGAGAGGTGATGTGCTGAGCAGCGG 1550      1560      1570      1580      1590      1600      1610
    GTCTTGCTCTGCTGCCTCTCGCGCCCGCGCAGCAGTGAGCAGCAGCAAGAGCAGTCTAGGGGGATCTACC
    CAGAACGAGACGACGGAGAGCGCGGGCGCGTCGTCACTCGTCGTCGTTCTCGTCAGATCCCCCTAGATGG
```

FIG. 5B

```
         1620        1630        1640        1650        1660
ATG AGC CCA GAA CGA CGC CCG GCC GAC ATC CGC CGT GCC ACC GAG GCG GAC ATG
TAC TCG GGT CTT GCT GCG GGC CGG CTG TAG GCG GCA CGG TGG CTC CGC CTG TAC
 M   S   P   E   R   R   P   A   D   I   R   R   A   T   E   A   D   M>
___a___a___a___a___a___a___a___BAR GENE____a___a___a___a___a___a___a___>

1670        1680        1690        1700        1710
CCG GCG GTC TGC ACC ATC GTC AAC CAC TAC ATC GAG ACA AGC ACG GTC AAC TTC
GGC CGC CAG ACG TGG TAG CAG TTG GTG ATG TAG CTC TGT TCG TGC CAG TTG AAG
 P   A   V   C   T   I   V   N   H   Y   I   E   T   S   T   V   N   F>
___a___a___a___a___a___a___a___BAR GENE____a___a___a___a___a___a___a___>

1720        1730        1740        1750        1760
1770
CGT ACC GAG CCG CAG GAA CCG CAG GAG TGG ACG GAC GAC CTC GTC CGT CTG CGG
GCA TGG CTC GGC GTC CTT GGC GTC CTC ACC TGC CTG CTG GAG CAG GCA GAC GCC
 R   T   E   P   Q   E   P   Q   E   W   T   D   D   L   V   R   L   R>
___a___a___a___a___a___a___a___BAR GENE____a___a___a___a___a___a___a___>

1780        1790        1800        1810        1820
GAG CGC TAT CCC TGG CTC GTC GCC GAG GTG GAC GGC GAG GTC GCC GGC ATC GCC
CTC GCG ATA GGG ACC GAG CAG CGG CTC CAC CTG CCG CTC CAG CGG CCG TAG CGG
 E   R   Y   P   W   L   V   A   E   V   D   G   E   V   A   G   I   A>
___a___a___a___a___a___a___a___BAR GENE____a___a___a___a___a___a___a___>

1830        1840        1850        1860        1870        1880
TAC GCG GGC CCC TGG AAG GCA CGC AAC GCC TAC GAC TGG ACG GCC GAG TCG ACC
ATG CGC CCG GGG ACC TTC CGT GCG TTG CGG ATG CTG ACC TGC CGG CTC AGC TGG
 Y   A   G   P   W   K   A   R   N   A   Y   D   W   T   A   E   S   T>
___a___a___a___a___a___a___a___BAR GENE____a___a___a___a___a___a___a___>

1890        1900        1910        1920        1930
GTG TAC GTC TCC CCC CGC CAC CAG CGG ACG GGA CTG GGC TCC ACG CTC TAC ACC
CAC ATG CAG AGG GGG GCG GTG GTC GCC TGC CCT GAC CCG AGG TGC GAG ATG TGG
 V   Y   V   S   P   R   H   Q   R   T   G   L   G   S   T   L   Y   T>
___a___a___a___a___a___a___a___BAR GENE____a___a___a___a___a___a___a___>

1940        1950        1960        1970        1980
CAC CTG CTG AAG TCC CTG GAG GCA CAG GGC TTC AAG AGC GTG GTC GCT GTC ATC
GTG GAC GAC TTC AGG GAC CTC CGT GTC CCG AAG TTC TCG CAC CAG CGA CAG TAG
 H   L   L   K   S   L   E   A   Q   G   F   K   S   V   V   A   V   I>
___a___a___a___a___a___a___a___BAR GENE____a___a___a___a___a___a___a___>

1990        2000        2010        2020        2030
2040
GGG CTG CCC AAC GAC CCG AGC GTG CGC ATG CAC GAG GCG CTC GGA TAT GCC CCC
CCC GAC GGG TTG CTG GGC TCG CAC GCG TAC GTG CTC CGC GAG CCT ATA CGG GGG
 G   L   P   N   D   P   S   V   R   M   H   E   A   L   G   Y   A   P>
___a___a___a___a___a___a___a___BAR GENE____a___a___a___a___a___a___a___>
```

FIG. 5C

```
       2050        2060        2070        2080        2090
CGC GGC ATG CTG CGG GCG GCC GGC TTC AAG CAC GGG AAC TGG CAT GAC GTG GGT
GCG CCG TAC GAC GCC CGC CGG CCG AAG TTC GTG CCC TTG ACC GTA CTG CAC CCA
 R   G   M   L   R   A   A   G   F   K   H   G   N   W   H   D   V   G>
___a___a___a___a___a___a___a__BAR GENE___a___a___a___a___a___a___a___>

2100        2110        2120        2130        2140        2150
TTC TGG CAG CTG GAC TTC AGC CTG CCG GTA CCG CCC CGT CCG GTC CTG CCC GTC
AAG ACC GTC GAC CTG AAG TCG GAC GGC CAT GGC GGG GCA GGC CAG GAC GGG CAG
 F   W   Q   L   D   F   S   L   P   V   P   P   R   P   V   L   P   V>
___a___a___a___a___a___a___a__BAR GENE___a___a___a___a___a___a___a___>

2160        2170
ACC GAG ATC TGA TGACCCTC
TGG CTC TAG ACT ACTGGGAG
 T   E   I   *>
___BAR GENE____>

>NOS_Terminator 2180      2190      2200      2210      2220      2230      2240
GAGTCTAGACGCGTCCCGAATTTCCCCGATCGTTCAAACATTTGGCAATAAAGTTTCTTAAGATTGAATC
CTCAGATCTGCGCAGGGCTTAAAGGGGCTAGCAAGTTTGTAAACCGTTATTTCAAAGAATTCTAACTTAG 2250      2260      2270      2280      2290      2300      2310
CTGTTGCCGGTCTTGCGATGATTATCATATAATTTCTGTTGAATTACGTTAAGCATGTAATAATTAACAT
GACAACGGCCAGAACGCTACTAATAGTATATTAAAGACAACTTAATGCAATTCGTACATTATTAATTGTA 2320      2330      2340      2350      2360      2370      2380
GTAATGCATGACGTTATTTATGAGATGGGTTTTTATGATTAGAGTCCCGCAATTATACATTTAATACGCG
CATTACGTACTGCAATAAATACTCTACCCAAAAATACTAATCTCAGGGCGTTAATATGTAAATTATGCGC 2390      2400      2410      2420      2430      2440      2450
ATAGAAAACAAAATATAGCGCGCAAACTAGGATAAATTATCGCGCGCGGTGTCATCTATGTTACTAGATC
TATCTTTTGTTTTATATCGCGCGTTTGATCCTATTTAATAGCGCGCGCCACAGTAGATACAATGATCTAG 2460      2470      2480      2490      2500      2510      2520
GGGAATTCGATATCAAGCTTATCGATACCGTCGACCTCGAGGGGGGGCCCGGTACCCAGCTTTTGTTCCC
CCCTTAAGCTATAGTTCGAATAGCTATGGCAGCTGGAGCTCCCCCCCGGGCCATGGGTCGAAAACAAGGG 2530      2540      2550      2560      2570      2580      2590
TTTAGTGAGGGTTAATTTCGAGCTTGGCGTAATCATGGTCATAGCTGTTTCCTGTGTGAATTGTTATCC
AAATCACTCCCAATTAAAGCTCGAACCGCATTAGTACCAGTATCGACAAAGGACACACTTTAACAATAGG 2600      2610      2620      2630      2640      2650      2660
GCTCACAATTCCACACAACATACGAGCCGGAAGCATAAAGTGTAAAGCCTGGGGTGCCTAATGAGTGAGC
CGAGTGTTAAGGTGTGTTGTATGCTCGGCCTTCGTATTTCACATTTCGGACCCCACGGATTACTCACTCG
```

FIG. 5D

```
       2670      2680      2690      2700      2710      2720      2730
TAACTCACATTAATTGCGTTGCGCTCACTGCCCGCTTTCCAGTCGGGAAACCTGTCGTGCCAGCTGCATT
ATTGAGTGTAATTAACGCAACGCGAGTGACGGGCGAAAGGTCAGCCCTTTGGACAGCACGGTCGACGTAA 2740      2750      2760      2770      2780      2790      2800
AATGAATCGGCCAACGCGCGGGGAGAGGCGGTTTGCGTATTGGGCGCTCTTCCGCTTCCTCGCTCACTGA
TTACTTAGCCGGTTGCGCGCCCCTCTCCGCCAAACGCATAACCCGCGAGAAGGCGAAGGAGCGAGTGACT 2810      2820      2830      2840      2850      2860      2870
CTCGCTGCGCTCGGTCGTTCGGCTGCGGCGAGCGGTATCAGCTCACTCAAAGGCGGTAATACGGTTATCC
GAGCGACGCGAGCCAGCAAGCCGACGCCGCTCGCCATAGTCGAGTGAGTTTCCGCCATTATGCCAATAGG 2880      2890      2900      2910      2920      2930      2940
ACAGAATCAGGGGATAACGCAGGAAAGAACATGTGAGCAAAAGGCCAGCAAAAGGCCAGGAACCGTAAAA
TGTCTTAGTCCCCTATTGCGTCCTTTCTTGTACACTCGTTTTCCGGTCGTTTTCCGGTCCTTGGCATTTT 2950      2960      2970      2980      2990      3000      3010
AGGCCGCGTTGCTGGCGTTTTTCCATAGGCTCCGCCCCCCTGACGAGCATCACAAAAATCGACGCTCAAG
TCCGGCGCAACGACCGCAAAAAGGTATCCGAGGCGGGGGGACTGCTCGTAGTGTTTTTAGCTGCGAGTTC 3020      3030      3040      3050      3060      3070      3080
TCAGAGGTGGCGAAACCCGACAGGACTATAAAGATACCAGGCGTTTCCCCCTGGAAGCTCCCTCGTGCGC
AGTCTCCACCGCTTTGGGCTGTCCTGATATTTCTATGGTCCGCAAAGGGGGACCTTCGAGGGAGCACGCG 3090      3100      3110      3120      3130      3140      3150
TCTCCTGTTCCGACCCTGCCGCTTACCGGATACCTGTCCGCCTTTCTCCCTTCGGGAAGCGTGGCGCTTT
AGAGGACAAGGCTGGGACGGCGAATGGCCTATGGACAGGCGGAAAGAGGGAAGCCCTTCGCACCGCGAAA 3160      3170      3180      3190      3200      3210      3220
CTCATAGCTCACGCTGTAGGTATCTCAGTTCGGTGTAGGTCGTTCGCTCCAAGCTGGGCTGTGTGCACGA
GAGTATCGAGTGCGACATCCATAGAGTCAAGCCACATCCAGCAAGCGAGGTTCGACCCGACACACGTGCT 3230      3240      3250      3260      3270      3280      3290
ACCCCCGTTCAGCCCGACCGCTGCGCCTTATCCGGTAACTATCGTCTTGAGTCCAACCCGGTAAGACAC
TGGGGGCAAGTCGGGCTGGCGACGCGGAATAGGCCATTGATAGCAGAACTCAGGTTGGGCCATTCTGTG 3300      3310      3320      3330      3340      3350      3360
GACTTATCGCCACTGGCAGCAGCCACTGGTAACAGGATTAGCAGAGCGAGGTATGTAGGCGGTGCTACAG
CTGAATAGCGGTGACCGTCGTCGGTGACCATTGTCCTAATCGTCTCGCTCCATACATCCGCCACGATGTC 3370      3380      3390      3400      3410      3420      3430
AGTTCTTGAAGTGGTGGCCTAACTACGGCTACACTAGAAGGACAGTATTTGGTATCTGCGCTCTGCTGAA
TCAAGAACTTCACCACCGGATTGATGCCGATGTGATCTTCCTGTCATAAACCATAGACGCGAGACGACTT 3440      3450      3460      3470      3480      3490      3500
GCCAGTTACCTTCGGAAAAAGAGTTGGTAGCTCTTGATCCGGCAAACAAACCACCGCTGGTAGCGGTGGT
CGGTCAATGGAAGCCTTTTTCTCAACCATCGAGAACTAGGCCGTTTGTTTGGTGGCGACCATCGCCACCA
```

FIG. 5E

```
       3510      3520      3530      3540      3550      3560      3570
TTTTTTGTTTGCAAGCAGCAGATTACGCGCAGAAAAAAAGGATCTCAAGAAGATCCTTTGATCTTTTCTA
AAAAAACAAACGTTCGTCGTCTAATGCGCGTCTTTTTTTCCTAGAGTTCTTCTAGGAAACTAGAAAAGAT 3580      3590      3600      3610      3620      3630      3640
CGGGGTCTGACGCTCAGTGGAACGAAAACTCACGTTAAGGGATTTTGGTCATGAGATTATCAAAAAGGAT
GCCCCAGACTGCGAGTCACCTTGCTTTTGAGTGCAATTCCCTAAAACCAGTACTCTAATAGTTTTTCCTA 3650      3660      3670      3680      3690      3700      3710
CTTCACCTAGATCCTTTTAAATTAAAAATGAAGTTTTAAATCAATCTAAAGTATATATGAGTAAACTTGG
GAAGTGGATCTAGGAAAATTTAATTTTTACTTCAAAATTTAGTTAGATTTCATATATACTCATTTGAACC 3720      3730      3740      3750      3760      3770      3780
TCTGACAGTTACCAATGCTTAATCAGTGAGGCACCTATCTCAGCGATCTGTCTATTTCGTTCATCCATAG
AGACTGTCAATGGTTACGAATTAGTCACTCCGTGGATAGAGTCGCTAGACAGATAAAGCAAGTAGGTATC 3790      3800      3810      3820      3830      3840      3850
TTGCCTGACTCCCCGTCGTGTAGATAACTACGATACGGGAGGGCTTACCATCTGGCCCCAGTGCTGCAAT
AACGGACTGAGGGGCAGCACATCTATTGATGCTATGCCCTCCCGAATGGTAGACCGGGGTCACGACGTTA 3860      3870      3880      3890      3900      3910      3920
GATACCGCGAGACCCACGCTCACCGGCTCCAGATTTATCAGCAATAAACCAGCCAGCCGGAAGGGCCGAG
CTATGGCGCTCTGGGTGCGAGTGGCCGAGGTCTAAATAGTCGTTATTTGGTCGGTCGGCCTTCCCGGCTC 3930      3940      3950      3960      3970      3980      3990
CGCAGAAGTGGTCCTGCAACTTTATCCGCCTCCATCCAGTCTATTAATTGTTGCCGGGAAGCTAGAGTAA
GCGTCTTCACCAGGACGTTGAAATAGGCGGAGGTAGGTCAGATAATTAACAACGGCCCTTCGATCTCATT 4000      4010      4020      4030      4040      4050      4060
GTAGTTCGCCAGTTAATAGTTTGCGCAACGTTGTTGCCATTGCTACAGGCATCGTGGTGTCACGCTCGTC
CATCAAGCGGTCAATTATCAAACGCGTTGCAACAACGGTAACGATGTCCGTAGCACCACAGTGCGAGCAG 4070      4080      4090      4100      4110      4120      4130
GTTTGGTATGGCTTCATTCAGCTCCGGTTCCCAACGATCAAGGCGAGTTACATGATCCCCCATGTTGTGC
CAAACCATACCGAAGTAAGTCGAGGCCAAGGGTTGCTAGTTCCGCTCAATGTACTAGGGGGTACAACACG 4140      4150      4160      4170      4180      4190      4200
AAAAAAGCGGTTAGCTCCTTCGGTCCTCCGATCGTTGTCAGAAGTAAGTTGGCCGCAGTGTTATCACTCA
TTTTTTCGCCAATCGAGGAAGCCAGGAGGCTAGCAACAGTCTTCATTCAACCGGCGTCACAATAGTGAGT 4210      4220      4230      4240      4250      4260      4270
TGGTTATGGCAGCACTGCATAATTCTCTTACTGTCATGCCATCCGTAAGATGCTTTTCTGTGACTGGTGA
ACCAATACCGTCGTGACGTATTAAGAGAATGACAGTACGGTAGGCATTCTACGAAAAGACACTGACCACT 4280      4290      4300      4310      4320      4330      4340
GTACTCAACCAAGTCATTCTGAGAATAGTGTATGCGGCGACCGAGTTGCTCTTGCCCGGCGTCAATACGG
CATGAGTTGGTTCAGTAAGACTCTTATCACATACGCCGCTGGCTCAACGAGAACGGGCCGCAGTTATGCC
```

FIG. 5F

```
       4350      4360      4370      4380      4390      4400      4410
GATAATACCGCGCCACATAGCAGAACTTTAAAAGTGCTCATCATTGGAAAACGTTCTTCGGGGCGAAAAC
CTATTATGGCGCGGTGTATCGTCTTGAAATTTTCACGAGTAGTAACCTTTTGCAAGAAGCCCCGCTTTTG 4420      4430      4440      4450      4460      4470      4480
TCTCAAGGATCTTACCGCTGTTGAGATCCAGTTCGATGTAACCCACTCGTGCACCCAACTGATCTTCAGC
AGAGTTCCTAGAATGGCGACAACTCTAGGTCAAGCTACATTGGGTGAGCACGTGGGTTGACTAGAAGTCG 4490      4500      4510      4520      4530      4540      4550
ATCTTTTACTTTCACCAGCGTTTCTGGGTGAGCAAAAACAGGAAGGCAAAATGCCGCAAAAAAGGGAATA
TAGAAAATGAAAGTGGTCGCAAAGACCCACTCGTTTTGTCCTTCCGTTTTACGGCGTTTTTTCCCTTAT 4560      4570      4580      4590      4600      4610      4620
AGGGCGACACGGAAATGTTGAATACTCATACTCTTCCTTTTTCAATATTATTGAAGCATTTATCAGGGTT
TCCCGCTGTGCCTTTACAACTTATGAGTATGAGAAGGAAAAAGTTATAATAACTTCGTAAATAGTCCCAA 4630      4640      4650      4660      4670      4680      4690
ATTGTCTCATGAGCGGATACATATTTGAATGTATTTAGAAAAATAAACAAATAGGGGTTCCGCGCACATT
TAACAGAGTACTCGCCTATGTATAAACTTACATAAATCTTTTATTTGTTTATCCCCAAGGCGCGTGTAA

4700
TCCCCGAAAAGTGC
AGGGGCTTTTCACG
```

FIG. 5G

SEQUENCE LISTING

<160> NUMBER OF SEQ ID NOS: 14

<210> SEQ ID NO 1
<211> LENGTH: 955
<212> TYPE: DNA
<213> ORGANISM: Artificial Sequence
<220> FEATURE:

<223> OTHER INFORMATION: Gns9 promoter

<400> SEQUENCE: 1

```
ggatccaggg gacttaactt tagtccatat atttagacac taatttagag tattaaatat      60
aaattactta caaaactaat tcaataaatg aaagctaatt tgcgagacaa attttttatg     120
tttaattaat ccataattag agaatgttta ctgtagcatc acatagacta atcatggatt     180
aattaggctc aatagattcg tctcgtgaat tagtccaaga ttatggatgg attttattaa    240
tagtctacgt ttaatattta taattagtgt tcaaacatcc gatgtgatag ggacttaaaa    300
agtttagtcc catctaaaca gggccacagt ctatgtggag catgttcacc gaacaccgat    360
aaatattgca agcccagaa tgattttggt cccacatgcc agaaactacc acacccacat      420
ttcggttcat tttcagctca ggaaaatcgt ccaacaattt cagctcagga aattaaatcg    480
tccgagaaag gaacaagttt ggagccgttg ggatgagagc aattaggtca cgcttaacta    540
caagtacagt ctcattcatc gacattgatt agccagcaac taaccactta accccgagcc    600
agcccaagcg ctccgtacgt tcgttgggcc ccgccgcgc aggcggagac aacggtcatc      660
cggcgcgccg gtcgctctcc ctcgctcgca cggccgcacc acccacttcg ccacgaaccc    720
gacgcgagcg cgacgtgcat ctcccaacat ccccgccatt tcctccccac ccaaaaccaa    780
cccgcccgcg tgcggctggc ccactttaca gcgcctcacc tcccccaacc ataaatcccc    840
gcccttttcc ccccctctcc accactcacc acgctctcca ctacacgact cgtcgccgtc    900
ttgctctgct gcctctcgcg cccgcgcagc agtgagcagc agcaagagca gcaaa         955
```

<210> SEQ ID NO 2
<211> LENGTH: 2300
<212> TYPE: DNA
<213> ORGANISM: Artificial Sequence
<220> FEATURE:
<223> OTHER INFORMATION: synthetic construct

<400> SEQUENCE: 2

```
aactttagtc catatattta gacactaatt tagagtatta aatataaatt acttacaaaa     60
ctaattcaat aaatgaaagc taatttgcga gacaaatttt ttatgtttaa ttaatccata    120
attagagaat gtttactgta gcatcacata gactaatcat ggattaatta ggctcaatag    180
attcgtctcg tgaattagtc caagattatg gatggatttt attaatagtc tacgtttaat    240
atttataatt agtgttcaaa catccgatgt gatagggact taaaaagttt agtcccatct    300
aaacagggcc acagtctatg tggagcatgt tcaccgaaca ccgataaata ttgcaaagcc    360
cagaatgatt ttggtcccac atgccagaaa ctaccacacc cacatttcgg ttcattttca    420
gctcaggaaa atcgtccaac aatttcagct caggaaatta atcgtccga gaaggaaca      480
agtttggagc cgttgggatg agagcaatta ggtcacgctt aactacaagt acagtctcat    540
tcatcgacat tgattagcca gcaactaacc acttaacccc gagccagccc aagcgctccg    600
tacgttcgtt gggccccgc cgcgcaggcg gagacaacgg tcatccggcg cgccggtcgc     660
tctcctcgc tcgcacggcc gcaccaccca cttcgcacg aacccgacgc gagcgcgacg      720
tgcatctccc aacatccccg ccatttcctc cccacccaaa accaacccgc cgcgtgcgg    780
ctggcccact ttacagcgcc tcacctcccc aaccataaa tccccgccct tttcccccc      840
tctccaccac tcaccacgct ctccactaca cgactcgtcg ccgtcttgct ctgctgcctc    900
tcgcgcccgc gcagcagtga gcagcagcaa gagcagtcta gaactagtgg atcccggggg    960
gcaatgagat atgaaaaagc ctgaactcac cgcgacgtct gtcgagaagt ttctgatcga   1020
```

```
aaagttcgac agcgtctccg acctgatgca gctctcggag ggcgaagaat ctcgtgcttt    1080
cagcttcgat gtaggagggc gtggatatgt cctgcgggta aatagctgcg ccgatggttt    1140
ctacaaagat cgttatgttt atcggcactt tgcatcggcc gcgctcccga ttccggaagt    1200
gcttgacatt ggggaattca gcgagagcct gacctattgc atctcccgcc gtgcacaggg    1260
tgtcacgttg caagacctgc ctgaaaccga actgcccgct gttctgcagc cggtcgcgga    1320
ggccatggat gcgatcgctg cggccgatct tagccagacg agcgggttcg gcccattcgg    1380
accgcaagga atcggtcaat acactacatg gcgtgatttc atatgcgcga ttgctgatcc    1440
ccatgtgtat cactggcaaa ctgtgatgga cgacaccgtc agtgcgtccg tcgcgcaggc    1500
tctcgatgag ctgatgcttt gggccgagga ctgccccgaa gtccggcacc tcgtgcacgc    1560
ggatttcggc tccaacaatg tcctgacgga caatggccgc ataacagcgg tcattgactg    1620
gagcgaggcg atgttcgggg attcccaata cgaggtcgcc aacatcttct tctggaggcc    1680
gtggttggct tgtatggagc agcagacgcg ctacttcgag cggaggcatc cggagcttgc    1740
aggatcgccg cggctccggg cgtatatgct ccgcattggt cttgaccaac tctatcagag    1800
cttggttgac ggcaatttcg atgatgcagc ttgggcgcag ggtcgatgcg acgcaatcgt    1860
ccgatccgga gccgggactg tcgggcgtac acaaatcgcc cgcagaagcg cggccgtctg    1920
gaccgatggc tgtgtagaag tactcgccga tagtggaaac cgacgcccca gcactcgtcc    1980
gggatccccc ctacgcaacc cgggagaaaa tctgagcgca cgatgacgag actctcagtt    2040
tagcagattt aacctgcgat tttaccctg accggtatac gtatatacgt gccggcaacg    2100
agctgtatcc gatccgaatt acggatgcaa ttgtccacga agtacttcct ccgtaaataa    2160
agtaggatca gggacataca tttgtatggt tttacgaata atgctatgca ataaaatttg    2220
cactgcttaa tgcttatgca ttttttgcttg gttcgattgt actggtgaat tattgttact    2280
gttcttttta cttctcgaat                                                 2300
```

<210> SEQ ID NO 3
<211> LENGTH: 566
<212> TYPE: DNA
<213> ORGANISM: Artificial Sequence
<220> FEATURE:
<223> OTHER INFORMATION: synthetic construct

<400> SEQUENCE: 3

```
ccatggctag cccagaaaga agaccggccg atattagacg tgctacagaa gctgatatgc      60
cagcagtttg tacaattgtt aatcattata tagaaacaag taccgtaaac tttcgaactg     120
aacctcaaga acctcaagaa tggactgatg atttagtccg tttacgagag cgctatcctt     180
ggcttgtagc agaagttgac ggagaagtag ctgggattgc atatgcgggc ccgtggaaag     240
cacgaaatgc atatgattgg acggctgaat caactgtgta cgtttcacca cgtcatcaac     300
ggacaggact tggttctact ttatataccc atctactgaa atctttggag gcacagggtt     360
ttaagagtgt ggtagctgtt ataggattgc cgaatgatcc ctcggtacgc atgcacgaag     420
ctctcggata tgctcccaga ggtatgttga gggccgcagg tttcaaacat ggaaattggc     480
atgatgtagg ttttttggcaa cttgacttct ctttaccagt acctcctcgt cccgttttac     540
ccgttactga gatctgatga tctaga                                          566
```

<210> SEQ ID NO 4
<211> LENGTH: 4704
<212> TYPE: DNA

<213> ORGANISM: Artificial Sequence
<220> FEATURE:
<223> OTHER INFORMATION: pAPI291 plasmid

<400> SEQUENCE: 4

```
cacctaaatt gtaagcgtta atatttgtt aaaattcgcg ttaaattttt gttaaatcag      60
ctcattttt aaccaatagg ccgaaatcgg caaaatccct tataaatcaa agaatagac     120
cgagataggg ttgagtgttg ttccagtttg gaacaagagt ccactattaa agaacgtgga    180
ctccaacgtc aaagggcgaa aaaccgtcta tcagggcgat ggcccactac gtgaaccatc    240
accctaatca gtttttttgg ggtcgaggtg ccgtaaagca ctaaatcgga accctaaagg    300
gagccccga tttagagctt gacggggaaa gccggcgaac gtggcgagaa aggaagggaa    360
gaaagcgaaa ggagcgggcg ctagggcgct ggcaagtgta gcggtcacgc tgcgcgtaac    420
caccacaccc gccgcgctta atgcgccgct acagggcgcg tcccattcgc cattcaggct    480
gcgcaactgt tgggaagggc gatcggtgcg ggcctcttcg ctattacgcc agctggcgaa    540
aggggatgt gctgcaaggc gattaagttg ggtaacgcca gggttttccc agtcacgacg    600
ttgtaaaacg acggccagtg aattgtaata cgactcacta tagggcgaat tggagctcaa    660
ctttagtcca tatttagga cactaattta gagtattaaa tataaattac ttacaaaact    720
aattcaataa atgaaagcta atttgcgaga caatttttt atgtttaatt aatccataat    780
tagagaatgt ttactgtagc atcacataga ctaatcatgg attaattagg ctcaatagat    840
tcgtctcgtg aattagtcca agattatgga tggattttat taatagtcta cgtttaatat    900
ttataattag tgttcaaaca tccgatgtga tagggactta aaaagtttag tcccatctaa    960
acagggccac agtctatgtg gagcatgttc accgaacacc gataaatatt gcaaagccca   1020
gaatgatttt ggtcccacat gccagaaact accacaccca catttcggtt cattttcagc   1080
tcaggaaaat cgtccaacaa tttcagctca ggaaattaaa tcgtccgaga aaggaacaag   1140
tttggagccg ttgggatgag agcaattagg tcacgcttaa ctacaagtac agtctcattc   1200
atcgacattg attagccagc aactaaccac ttaaccccga gccagcccaa gcgctccgta   1260
cgttcgttgg gccccgccg cgcaggcgga gacaacggtc atccggcgcg ccggtcgctc   1320
tccctcgctc gcacggccgc accacccact tcgccacgaa cccgacgcga gcgcgacgtg   1380
catctcccaa catccccgcc atttcctccc cacccaaaac caacccgccc gcgtgcggct   1440
ggcccacttt acagcgcctc acctccccca accataaatc cccgcccttt tccccccctc   1500
tccaccactc accacgctct ccactacacg actcgtcgcc gtcttgctct gctgcctctc   1560
gcgcccgcgc agcagtgagc agcagcaaga gcagtctagg gggatctacc atgagcccag   1620
aacgacgccc ggccgacatc cgccgtgcca ccgaggcgga catgccggcg gtctgcacca   1680
tcgtcaacca ctacatcgag acaagcacgg tcaacttccg taccgagccg caggaaccgc   1740
aggagtggac ggacgacctc gtccgtctgc gggagcgctc tccctggctc gtcgccgagg   1800
tggacggcga ggtcgccggc atcgcctacg cgggcccctg gaaggcacgc aacgcctacg   1860
actgacggc cgagtcgacc gtgtacgtct cccccgcca ccagcggacg ggactgggct   1920
ccacgctcta cacccacctg ctgaagtccc tggaggcaca gggcttcaag agcgtggtcg   1980
ctgtcatcgg gctgcccaac gacccgagcg tgcgcatgca cgaggcgctc ggatatgccc   2040
cccgcggcat gctgcgggcg gccggcttca gcacgggaa ctggcatgac gtgggtttct   2100
ggcagctgga cttcagcctg ccggtaccgc ccgtccggt cctgcccgtc accgagatct   2160
gatgaccctc gagtctagac gcgtcccgaa tttcccccgat cgttcaaaca tttggcaata   2220
```

-continued

```
aagtttctta agattgaatc ctgttgccgg tcttgcgatg attatcatat aatttctgtt    2280
gaattacgtt aagcatgtaa taattaacat gtaatgcatg acgttattta tgagatgggt    2340
ttttatgatt agagtcccgc aattatacat ttaatacgcg atagaaaaca aaatatagcg    2400
cgcaaactag gataaattat cgcgcgcggt gtcatctatg ttactagatc gggaattcga    2460
tatcaagctt atcgataccg tcgacctcga ggggggggccc ggtacccagc ttttgttccc    2520
tttagtgagg gttaatttcg agcttggcgt aatcatggtc atagctgttt cctgtgtgaa    2580
attgttatcc gctcacaatt ccacacaaca tacgagccgg aagcataaag tgtaaagcct    2640
ggggtgccta atgagtgagc taactcacat taattgcgtt gcgctcactg cccgctttcc    2700
agtcgggaaa cctgtcgtgc cagctgcatt aatgaatcgg ccaacgcgcg gggagaggcg    2760
gtttgcgtat tgggcgctct tccgcttcct cgctcactga ctcgctgcgc tcggtcgttc    2820
ggctgcggcg agcggtatca gctcactcaa aggcggtaat acggttatcc acagaatcag    2880
gggataacgc aggaaagaac atgtgagcaa aaggccagca aaaggccagg aaccgtaaaa    2940
aggccgcgtt gctggcgttt ttccataggc tccgcccccc tgacgagcat cacaaaaatc    3000
gacgctcaag tcagaggtgg cgaaacccga caggactata aagataccag gcgtttcccc    3060
ctggaagctc cctcgtgcgc tctcctgttc cgaccctgcc gcttaccgga tacctgtccg    3120
cctttctccc ttcgggaagc gtggcgcttt ctcatagctc acgctgtagg tatctcagtt    3180
cggtgtaggt cgttcgctcc aagctgggct gtgtgcacga accccccgtt cagcccgacc    3240
gctgcgcctt atccggtaac tatcgtcttg agtccaaccc ggtaagacac gacttatcgc    3300
cactggcagc agccactggt aacaggatta gcagagcgag gtatgtaggc ggtgctacag    3360
agttcttgaa gtggtggcct aactacggct acactagaag gacagtattt ggtatctgcg    3420
ctctgctgaa gccagttacc ttcggaaaaa gagttggtag ctcttgatcc ggcaaacaaa    3480
ccaccgctgg tagcggtggt ttttttgttt gcaagcagca gattacgcgc agaaaaaaag    3540
gatctcaaga agatcctttg atcttttcta cggggtctga cgctcagtgg aacgaaaact    3600
cacgttaagg gattttggtc atgagattat caaaaaggat cttcacctag atccttttaa    3660
attaaaaatg aagttttaaa tcaatctaaa gtatatatga gtaaacttgg tctgacagtt    3720
accaatgctt aatcagtgag gcacctatct cagcgatctg tctatttcgt tcatccatag    3780
ttgcctgact ccccgtcgtg tagataacta cgatacggga gggcttacca tctggcccca    3840
gtgctgcaat gataccgcga gacccacgct caccggctcc agatttatca gcaataaacc    3900
agccagccgg aagggccgag cgcagaagtg gtcctgcaac tttatccgcc tccatccagt    3960
ctattaattg ttgccgggaa gctagagtaa gtagttcgcc agttaatagt ttgcgcaacg    4020
ttgttgccat tgctacaggc atcgtggtgt cacgctcgtc gtttggtatg gcttcattca    4080
gctccggttc ccaacgatca aggcgagtta catgatcccc catgttgtgc aaaaaagcgg    4140
ttagctcctt cggtcctccg atcgttgtca gaagtaagtt ggccgcagtg ttatcactca    4200
tggttatggc agcactgcat aattctctta ctgtcatgcc atccgtaaga tgcttttctg    4260
tgactggtga gtactcaacc aagtcattct gagaatagtg tatgcggcga ccgagttgct    4320
cttgcccggc gtcaatacgg gataataccg cgccacatag cagaacttta aaagtgctca    4380
tcattggaaa acgttcttcg gggcgaaaac tctcaaggat cttaccgctg ttgagatcca    4440
gttcgatgta acccactcgt gcacccaact gatcttcagc atcttttact ttcaccagcg    4500
tttctgggtg agcaaaaaca ggaaggcaaa atgccgcaaa aaagggaata agggcgacac    4560
```

-continued

```
ggaaatgttg aatactcata ctcttccttt ttcaatatta ttgaagcatt tatcagggtt     4620
attgtctcat gagcggatac atatttgaat gtatttagaa aaataaacaa atagggttc     4680 cgcgcacatt tccccgaaaa gtgc                                           4704
```

<210> SEQ ID NO 5
<211> LENGTH: 29
<212> TYPE: DNA
<213> ORGANISM: Artificial Sequence
<220> FEATURE:
<223> OTHER INFORMATION: primer

<400> SEQUENCE: 5

```
aacaatactg gaattcgaga agtaaaaag                                        29
```

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6

```
ctacgcaacc cgggagaaaa tc                                               22
```

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7

```
gacttaactt tagtcatatt tag                                              23
```

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8

```
ttcgctcttg ctgctgctca ct                                               22
```

<210> SEQ ID NO 9
<211> LENGTH: 49
<212> TYPE: DNA
<213> ORGANISM: Artificial Sequence
<220> FEATURE:
<223> OTHER INFORMATION: primer

<400> SEQUENCE: 9

```
gcagtctaga actagtagat ctcgggggc aacgaaatat gaaaaagcc                   49
```

<210> SEQ ID NO 10
<211> LENGTH: 49
<212> TYPE: DNA
<213> ORGANISM: Artificial Sequence
<220> FEATURE:
<223> OTHER INFORMATION: primer

<400> SEQUENCE: 10

```
ggcttttca tatttcgttg ccccccgaga tctactagtt ctagactgc                   49
```

```
<210> SEQ ID NO 11
<211> LENGTH: 47
<212> TYPE: DNA
<213> ORGANISM: Artificial Sequence
<220> FEATURE:
<223> OTHER INFORMATION: primer

<400> SEQUENCE: 11
taatggatcc tcattcctat tcctttgccc tcggacgagt gctgggg          47

<210> SEQ ID NO 12
<211> LENGTH: 26
<212> TYPE: DNA
<213> ORGANISM: Artificial Sequence
<220> FEATURE:
<223> OTHER INFORMATION: primer

<400> SEQUENCE: 12
atcgccgcgg ctccgggcgt atatgc          26

<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13
attgcaagcg aaccggaatt gccag          25

<210> SEQ ID NO 14
<211> LENGTH: 23
<212> TYPE: DNA
<213> ORGANISM: Artificial Sequence
<220> FEATURE:
<223> OTHER INFORMATION: Gns9 promoter

<400> SEQUENCE: 14
aaactcttcc tttttcaatt cag          23
```

PLANT SELECTABLE MARKER AND PLANT TRANSFORMATION METHOD

This application is a continuation-in-part of application Ser. No. 09/344,438, filed Jun. 25, 1999, now U.S. Pat. No. 6.284.956, which claims priority to U.S. Provisional Application Serial No. 60/090,896, filed on Jun. 25, 1998, all of which are hereby incorporated by reference in their entirety.

FIELD OF THE INVENTION

The present invention relates to an expression cassette containing a selectable marker gene, for cotransforming a monocot plant, to plant transformation methods using the selectable marker expression cassette, and to plants and plant cells transformed with the selectable marker expression cassette.

BACKGROUND OF THE INVENTION

Transgenic plants carrying one or more expressible heterologous genes in a transgene expression cassette have a variety of potential advantages. The plants carrying such a transgene expression cassette may carry one or more genes which confer herbicide tolerance, pesticide tolerance insect resistance, tolerance to stress, enhanced flavor or stability of the fruit or seed, or the ability to synthesize useful, non-plant proteins, e.g., medically valuable proteins or the ability to generate altered concentrations of plant proteins, and related impacts on the plant, e.g., altered levels of plant proteins catalyzing production of plant metabolites including secondary plant metabolites.

Ideally, the expression of the heterologous protein from the transgene expression cassette is largely confined to a particular differentiated plant tissue, e.g., the fruit or seed, and/or induced under selected conditions, e.g., plant hormone induction. To this end, it is desirable to place the gene encoding the heterologous protein in a gene expression cassette under the control of a promoter that is induced or inducible in a selected plant tissue, such as roots or leaves or seeds, and/or during selected plant induction states, such as seed maturation or seed germination.

There are multiple technologies, methods and biological materials that are needed in order to successfully genetically engineer a plant cell so that it can express recombinant molecules from a transgene expression cassette, and to make the transgenic plant cell commercially potentially usable and acceptable, including the following.

First, it is important to the success of methods used to transform plant cells to be able to readily and quickly detect successful transformant events. In the usual case, this means being able to screen cells for successful transformation within a few days to a few weeks of the transformation procedure. For many plants, including monocots, positive screening for successful transformants is performed most rapidly by co-transforming one or more transgene expression cassettes with a selectable marker expression cassette and conveniently by screening callus cells taken through the transformation process for a selectable marker in culture or on media plates.

The selectable marker gene in the selectable marker expression cassette is operably linked to selectable marker regulatory elements including a promoter and terminator. The expression in the transgenic plant cell of the selectable marker gene generally encodes a protein which confers resistance to an antibiotic or herbicide. Common selectable marker genes include, for example, the nptII kanamycin resistance gene, for selection in kanamycin-containing media, or the phosphinothricin acetyltransferase gene, for selection in media containing phosphinothricin (PPT), or the hph hygromycin phosphotransferase gene, for selection in media containing hygromycin B.

These selectable marker genes in the selectable marker expression cassette are expressed by promoters which are active in the undifferentiated callus tissues into which the selectable marker and heterologous genes are inserted. Heretofore, promoters generally used to drive expression of the selectable markers genes have been constitutive gene promoters, such as the Cauliflower Mosaic virus (CaMV) 35s promoter, the ubiquitin ubi1 promoter, and the actin promoter, have been constitutive promoters which express in a wide range of tissues, including the tissues in which expression of the heterologous gene is desired.

Second, it is important to the success of methods used to transform plant cells to be able to perform the transformation process in an efficient matter, that is, the process of plant cell transformation, selection and regeneration ought to require limited post-transformation manipulation of the plant tissue such as callus subjected to transformation, so as to enable processing of relevant number of transformed plant tissues so as to take advantage of items such as position effects.

Third, it may be important to the successful use and commercial acceptance of transgenic plant organs or tissues such as transgenic plant seeds in a food or feed formulation incorporating as ingredients transgenic plant seeds or extracts thereof, that the selectable marker protein not be present, or present only in very low amounts. In other words, the presence of the selectable marker protein in a transgenic seed for use in food or feed is potentially a negative or block to the food or feed use of said transgenic seed.

Finally, in many cases, it is useful to be able to simultaneously transform plant cells with one or more transgene expression cassettes. Such a procedure would allow the introduction of multiple transgenic traits in a single plant cell, e.g., multiple proteins promoting human or animal health in a single transgenic plant cell or transgenic plant tissue or organ such as a plant seed. Such a procedure would also allow for the introduction of multiple genes in a single plant transgenic plant cell with the intended purpose of using said genes in combination as a way to metabolically engineer a plant cell pathway, e.g., a pathway coding for plant secondary metabolites such as the phenylpropanoid pathway. Transformation and selection methods employing such promoters have generally not been successful and efficient in transforming monocot plants with multiple, e.g., 5–10, heterologous genes found in multiple transgene expression cassettes.

Heretofore, there have been no convenient methods, technologies and biological materials enabling efficient transformation events and selection and regeneration with the resulting transgenic plant tissues not expressing the selectable marker protein from the selectable marker expression cassette.

For example, the use of the double cassette vector or multiple single cassette vectors in conjunction with Agrobacterium transformation requires that the resulting transformants go through a breeding program in order to determine if it is possible to segregate the selectable marker expression cassette from the transgene expression cassette so as to get a transgenic plant and resulting seed carrying the transgene expression cassette but not the selectable marker expression cassette. This breeding program takes substantial time to the development of a product from a transgenic plant.

A similar problem is encountered with the use of the ballistic transformation methodology in which there is co-transformation of a selectable marker expression cassette with a constitutive promoter directing expression of the selectable marker gene, along with the transgene expression cassette. Again, in order to generate a transgenic plant cell and resulting transgenic plant or plant seed without the selectable marker protein, the selectable marker expression cassette and the transgenic expression cassette need to be genetically segregated using a breeding program, a timely procedure that limits the commercial utility transgenic protein.

The current invention solves these current problems. First, this invention includes a method of selecting and regenerating transgenic plants that significantly reduces the time and labor processing transgenic plant material. Second, the present invention includes a regulated promoter for use in controlling expression of the selectable marker gene during selection, but not after regeneration so that the resulting transgenic seed does not contain the selectable marker protein.

SUMMARY OF THE INVENTION

In one aspect, the invention includes a set of expression cassettes, including vectors containing expression cassettes, for use in transforming monocot plants with one or more heterologous genes capable of producing heterologous proteins in the monocot plant seeds, under selected induction conditions. The set includes: (a) a selectable marker expression cassette having, operatively linked in sequence in a 5' to 3' direction, (i) a regulated transcriptional regulatory region, (ii) a selectable marker gene, and (iii) a 3' untranslated terminator region; and (b) at least one heterologous gene expression cassette having, operatively linked in sequence in a 5' to 3' direction, (i) a transcriptional regulatory region that is induced or inducible in plant seeds, (ii) a first DNA sequence encoding a heterologous protein, and (iii) a 3' untranslated terminator region.

The regulated transcriptional regulatory region in the selectable marker expression cassette is one which expresses in transformed callus cells at a significantly higher level than in the selected target tissue, e.g., seeds, and hybridizes under conditions of high stringency with the rice beta-glucanase gene promoter Gns-9 identified by SEQ ID NO:1. The promoter may be contained in the sequence identified by SEQ ID NO:1.

The transcriptional regulatory region in the heterologous-gene expression cassette is preferably induced or inducible during seed maturation or seed germination.

For use in transforming monocot plants by a plurality of heterologous genes, the set of expression cassettes may include a plurality of heterologous-gene expression cassettes, each having, operatively linked in sequence in a 5' to 3' direction, (i) a transcriptional regulatory region that is induced or inducible in plant seeds, (ii) a DNA sequence encoding a heterologous protein, and (iii) a 3' untranslated terminator region.

Alternatively, the expression cassettes for the selectable marker gene and one or more heterologous proteins may be carried, e.g., in tandem, in a single plant-transformation vector.

In another aspect, the invention includes a method for transforming monocot plants with one or more heterologous genes capable of producing heterologous proteins in the monocot plant seeds, under selected induction conditions. The method includes transforming plant callus cells with the set of expression cassettes described above; culturing the callus cells in the presence of a selection agent effective to block growth of callus cells, in the absence of expression of the selectable marker gene; selecting those callus cells that express the selectable marker, as evidenced by their growth in the presence of the selection agent; and regenerating the selected callus cells into transgenic plants under non-selection conditions.

Using either the concatenated heterologous-gene expression cassette above, or a plurality of individual heterologous gene expression cassettes, the method is effective to transform monocot plants with a plurality of heterologous genes, e.g., four or more genes, and as many as ten or more genes.

Also disclosed are transgenic monocot plants produced by the method of the invention, by transformation of callus cells with the set of expression cassettes of the invention, and transgenic seeds produced by the plants.

In still another aspect, the invention includes a plant transformation expression cassette for transforming monocot plant cells with a selectable marker gene containing, operatively linked in sequence in a 5' to 3' direction, (i) a transcriptional regulatory region which hybridizes under high-stringency conditions with a rice beta-glucanase gene promoter identified by SEQ ID NO:1, and which expresses in callus cells at a significantly higher level than in a selected target tissue, (ii) a selectable marker gene, and (iii) a 3' untranslated terminator region.

In various embodiments, the selectable marker gene may include, but is not limited to, the nptII kanamycin resistance gene, for selection in kanamycin-containing media, or a gene encoding phosphinothricin acetyltransferase, for selection in media containing phosphinothricin, or a gene encoding hygromycin phosphotransferase (HPH), for selection in media containing hygromycin B. In a preferred embodiment, the selectable marker gene encodes HPH. In other embodiments, the 3' untranslated terminator region is the 3' untranslated region from the rice alpha-amylase 1A (RAmy1A) gene, and the marker gene expression cassette the sequence identified by SEQ ID NO:2.

The invention also includes a transgenic monocot plant seeds containing a heterologous selectable marker gene under the control of a regulatory region that is induced in callus plant tissue, allowing selection of transgenic monocot callus tissue in a suitable selection medium, but is substantially dormant in seed maturation or germination, preventing expression of the marker gene at gene-selection levels in seeds, and a heterologous protein that is under the control of a regulatory region that is induced during seed maturation or germination.

Also forming part of the invention is a transgenic monocot plant seed containing at least four different expression cassettes, each containing a regulatory region that is induced in maturing or germinating seeds, a gene encoding a protein heterologous to monocot plants, and (iii) a 3' untranslated terminator region, and characterized by detectable expression of the expression cassette genes during seed maturation of germination.

These and other objects and features of the invention will become more fully apparent when the following detailed description of the invention is read in conjunction with the accompanying drawings.

BRIEF DESCRIPTION OF THE DRAWINGS

FIGS. 5A–G provides the sequence of pAPI291 (GnS9-Bar), nucleotides 1 to 4704.

DETAILED DESCRIPTION OF THE INVENTION

Figure 1A:
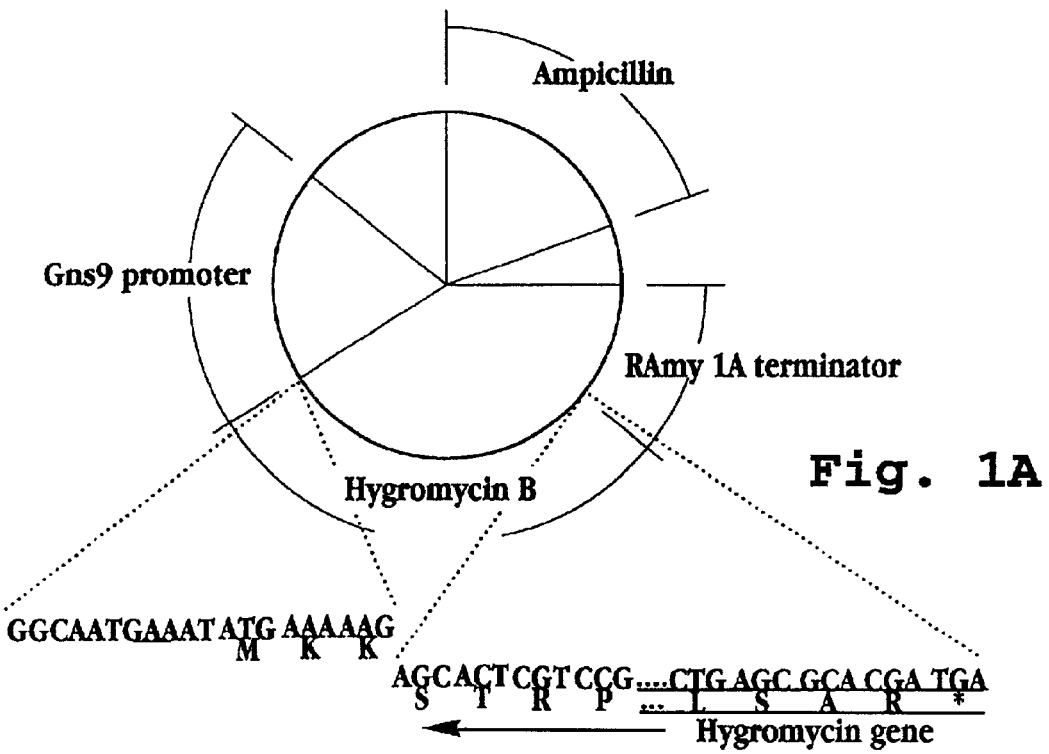
FIG. 1A shows the pAPI-76 selectable marker vector in accordance with one embodiment of the invention.

I. Definitions:

The terms below have the following meaning, unless indicated otherwise in the specification.

"Seed" means grain which includes the seed proper, the seed coat and/or the seed hull, or any portion thereof.

"Germination" refers to the breaking of dormancy in a seed and the resumption of metabolic activity in the seed, including the production of enzymes effective to break down starches in the seed endosperm.

"Seed maturation" or "grain development" refers to the period starting with fertilization in which metabolizable reserves, e.g., sugars, oligosaccharides, starch, phenolics, amino acids, and proteins, are deposited, with and without vacuole targeting, to various tissues in the seed (grain), e.g., endosperm, testa, aleurone layer, and scutellar epithelium, leading to grain enlargement, grain filling, and ending with grain desiccation.

A "regulatable" promoter is upregulated ("turned on" or "induced") or downregulated ("turned off") in response to a biochemical stimulus, such as the presence or absence of a small molecule, or in a particular tissue, e.g., callus tissue, root tissue, etc., or at a particular stage in plant development, e.g., undifferentiated callus cell vs differentiated plant tissue, or seed development stage, e.g., seed maturation or germination.

A "constitutive" promoter is a promoter which is absent of any regulation, i.e., is unregulated.

"Inducible or induced" refers to a promoter that is upregulated by the presence or absence of a small molecule, or is upregulated in a particular tissue (e.g., callus tissue, or root tissue, etc.) or at a particular stage in plant development (e.g., during seed maturation).

"Inducible or induced during seed germination" refers to a promoter which is or can be upregulated significantly (greater than 25%) during seed germination.

"Inducible during seed maturation" refers to a promoter which is or can be upregulated significantly (greater than 25%) during seed maturation.

A promoter is "substantially dormant" if the gene the promoter regulates is expressed at substantially undetectable levels. As the term applies to a promoter controlling the expression of a selectable marker gene, the promoter is substantially dormant if the amount of selectable marker produced is below a threshold that can be discriminated by subjecting the plant cell or tissue to a suitable selection pressure, e.g., an antibiotic. For example, in the case of a seed, the selectable-marker gene promoter would be considered dormant during seed germination if it was impossible to discriminate between transformed (containing the selectable marker gene) and non-transformed germinating seeds (not containing the selectable-marker gene) on the basis of the presence of a suitable selection pressure, e.g., antibiotic.

"Small molecules", in the context of promoter induction, are typically small organic or bioorganic molecules less than about 1 kilodalton. Examples of such small molecules include sugars, sugar-derivatives (including phosphate derivatives), and plant hormones (such as, gibberellic or absissic acid), and environmental gases, such as $O_2$.

"Heterologous DNA" or "foreign DNA" refers to DNA, and typically to a DNA coding sequence ("heterologous coding sequence"), which has been introduced into plant cells from another source, that is, a non-plant source or from another species of plants, or a same-species coding sequence which is placed under the control of a plant promoter that normally controls another coding sequence. An insulin coding sequence placed under the control of a plant promoter is an example of a heterologous DNA, as is a rice alpha-glucanase or beta-glucanase coding sequence placed under the control of a barley α-amylase promoter.

A "transcription regulatory region" or "promoter" refers to nucleic acid sequences that influence and/or promote initiation of transcription. Promoters are typically considered to include regulatory regions, such as enhancer or inducer elements.

"Operably linked" refers to components of an expression cassette, function as a unit to express a heterologous protein. For example, a promoter operably linked to a heterologous DNA, which encodes a protein, promotes the production of functional mRNA corresponding to the heterologous DNA.

A "chimeric gene" or "expression cassette" in the context of the present invention, refers to a promoter sequence operably linked to DNA sequence that encodes a gene product, e.g., a selectable marker gene, or a desired heterologous gene, and preferably a transcription terminator sequence. The cassette may also contain a signal peptide coding region operably linked between the promoter and the gene product coding sequence in translation-frame with the gene product coding sequence, and may further contain transcription regulatory elements, such as the above-noted transcription termination signals, as well as translation regulatory signals, such as, termination codons.

A DNA sequence is "derived from" a gene, such as a rice alpha-glucanase or beta-glucanase gene, if it corresponds in sequence to a segment or region of that gene. Segments of genes which may be derived from a gene include the promoter region, the 5' untranslated region, and the 3' untranslated region of the gene.

A "product" encoded by a DNA molecule includes, for example, RNA molecules and polypeptides.

"Stably transformed" refers to a cereal cell or plant that has foreign nucleic acid stably integrated into its genome which is transmitted through multiple generations.

"Cell culture" refers to cells and cell clusters, typically callus cells, growing on or suspended in a suitable growth medium.

"Sequence identity" refers to the degree of identity between two sequences when those sequences are aligned using the "LALIGN" sequence alignment program (or analogous program) using default parameters. "LALIGN" is found in the FASTA version 1.7 suite of sequence comparison programs (Pearson, et al., 1988; Pearson, 1990; program available from William R. Pearson, Department of Biological Chemistry, Box 440, Jordan Hall, Charlottesville, Va.).

When a first polynucleotide fragment or polypeptide fragment is said to "correspond to" a second polynucleotide fragment or polypeptide fragment, respectively, it means that the fragments or regions are essentially co-extensive with one another when the sequences representing the fragments are aligned using a sequence alignment program, such as "LALIGN" or "MACVECTOR" (IBI, New Haven, Conn.). "Corresponding" polynucleotide or polypeptide fragments typically contain a similar, if not identical, number of residues. It will be understood, however, that corresponding fragments may contain insertions or deletions of residues with respect to one another, as well as some differences in their sequences.

"Hybridization" includes any process by which a strand of a nucleic acid joins with a complementary nucleic acid strand through base-pairing. Thus, strictly speaking, the term refers to the ability of the complement of the target sequence to bind to the test sequence, or vice-versa.

"Hybridization conditions" are based on the melting temperature (Tm) of the nucleic acid binding complex or probe and are typically classified by degree of "stringency" of the conditions under which hybridization is measured. For example, "maximum stringency" typically occurs at about Tm-5° C. (5° below the Tm of the probe); "high stringency" at about 5–10° below the Tm; "intermediate stringency" at about 10–20° below the Tm of the probe; and "low stringency" at about 20–25° below the Tm. Functionally, maximum stringency conditions may be used to identify sequences having strict identity or near-strict identity with the hybridization probe; while high stringency conditions are used to identify sequences having about 80% or more sequence identity with the probe.

An example of "high stringency" conditions includes hybridization at about 65° C. in about 5× SSPE and washing conditions of about 65° C. in about 0.1× SSPE (where 1× SSPE=0.15 sodium chloride, 0.010 M sodium phosphate, and 0.001 M disodium EDTA).

Two nucleotide sequences are considered to be "functionally homologous" if they hybridize with one another under moderately stringent conditions, i.e. 0.1% SSC at room temperature. Typically, two homologous nucleotide sequences are greater than or equal to about 60% identical when optimally aligned using the ALIGN program (Dayhoff, M. O., in *ATLAS OF PROTEIN SEQUENCE AND STRUCTURE* (1972) Vol. 5, National Biomedical Research Foundation, pp. 101–110, and Supplement 2 to this volume, pp. 1–10.).

II. Selectable-Marker Expression Cassette

The present invention includes a monocot plant transformation expression cassette containing a selectable marker gene which expresses a selectable marker at a substantially higher level in transformed callus tissue than in the target tissue. The cassette includes, in a 5' to 3' direction, (i) a transcriptional regulatory region, or promoter, which is a regulated promoter (ii) the selectable marker gene, and (iii) a 3' untranslated terminator region.

The cassette may be carried in a suitable vector, e.g., cloning vector or plant-transformation vector. This vector may additionally include, e g, in tandem with the selectable marker cassette, one or more expression cassettes for expressing heterologous genes, for example, in maturing or germinating monocot plant seeds.

A. Transcription Regulatory Region

The transcriptional regulatory region, or promoter, is a regulated promoter which expresses in callus tissue at significantly higher levels than in selected target plant tissue. One preferred promoter is the rice beta-glucanase-9 (Gns9) promoter. The Gns9 promoter, together with several other rice alpha-glucanase or beta-glucanase promoters, have been described in U.S. patent application Ser. No. 09/105,390, filed Jun. 25, 1998, which is incorporated by reference, now U.S. Pat. No. 6,288,303.

In a preferred embodiment, the transcriptional regulatory region has a nucleotide sequence which is effective to hybridize under high-stringency conditions to the Gns9 promoter having the sequence SEQ ID NO:1. In various other embodiments, the transcriptional regulatory region has a nucleotide sequence having at least 80% identity, preferably 90% identity, more preferably 95% identity, to the Gns9 promoter having the sequence SEQ ID NO:1.

In another embodiment, the transcriptional regulatory region has the Gns9 promoter sequence contained in SEQ ID NO:1. This promoter may include the entire sequence in SEQ ID NO:1, or operative portions thereof, as identified, for example, by conventional deletion analysis, in which a series of 5'-end deletions or 3'-end deletions, or internal deletions of SEQ ID NO:1 are made, and tested for the ability to promoter the expression of a selectable marker in, for example, transformed callus tissue, as described below.

B. Selectable Marker Gene

A general review of suitable markers for the members of the grass family is found in Wilmink and Dons (1993) *Plant Mol. Biol. Reptr*, 11(2):165–185. Common selectable marker genes include, for example, the nptII kanamycin resistance gene, for selection in kanamycin-containing media, or the phosphinothricin acetyltransferase gene, for selection in media containing phosphinothricin (PPT), or the hph hygromycin phosphotransferase gene, for selection in media containing hygromycin B. In a preferred embodiment, a sequence encoding hygromycin phosphotransferase is used, and selection is performed in the presence of hygromycin B.

C. 3' Untranslated Terminator Region

The expression cassette typically has a transcriptional termination region at the opposite end from the transcription initiation regulatory region. The transcriptional termination region may normally be associated with the transcriptional initiation region or from a different gene. The transcriptional termination region may be selected, particularly for stability of the mRNA to enhance expression. Illustrative transcriptional termination regions include the NOS terminator from Agrobacterium Ti plasmid and the rice α-amylase RAmy1A terminator.

The selectable-marker cassette may be constructed according to standard recombinant construction methods such as outlined in U.S. Pat. Nos. 5,889,189 and 5,888,789, which are incorporated herein by reference.

III. Heterologous Gene Expression Cassette

The invention also contemplates, for co-transformation of monocot plants, a heterologous-protein expression cassette capable of expressing a desired heterologous protein in transformed plants. The cassette is preferably one that is inducible in monocot seeds during maturation or germination.

A. Heterologous Gene.

The cassette preferably includes, (i) a heterologous gene coding sequence for a selected protein of interest, (ii) upstream of the coding sequence, a monocot promoter which is induced or inducible during maturation or germination of a monocot seed, and (iii) a 3' termination sequence like that described above.

Typical proteins which are encoded by the heterologous gene include commercially important therapeutic proteins and polypeptides, including erythropoietin (EPO), tissue plasminogen activator (t-PA), urokinase and prourokinase, growth hormones, cytokines, factor VIII, epoetin-α, granulocyte colony stimulating factor, and vaccines. The coding sequence for the mature forms of these proteins are available from a variety of reference and sequence database sources.

Other heterologous proteins include polypeptides that form immunologically active epitopes, and enzymes which catalyze the conversion of intracellular metabolites, with the consequent buildup of selected metabolites in the cells. One group of proteins for use in the invention include enzymes for starch biosynthesis, including ADP glucosepyrophosphorylase (EC2.7.7.27), starch synthase (EC 2.4.1.21), and branching enzyme (R,Q). More generally, the heterologous proteins may be derived from either plant or animal sources.

B. Induced or Inducible Promoters.

Promoters that are induced or inducible during germination include the promoters from the rice α-amylase RAmy1A, RAmy1B, RAmy2A, RAmy3A, RAmy3B, RAmy3C, RAmy3D, and RAmy3E genes, and from the pM/C, gKAmy141, gKAmy155, Amy32b, and HV18 barley α-amylase genes. These promoters are described, for example, in *ADVANCES IN PLANT BIOTECHNOLOGY*, Ryu, et al, Eds., Elsevier, Amsterdam, 1994, p.37, and references cited therein.

Representative promoters that are induced or inducible during seed-maturation conditions include those associated with the following monocot storage proteins: rice glutelins, oryzins, and prolamines, barley hordeins, wheat gliadins and glutelins, maize zeins and glutelins, oat glutelins, and sorghum kafirins, millet pennisetins, and rye secalins. One preferred promoter for expression in maturing seeds is the barley endosperm-specific B1-hordein promoter (Brandt, A., et al., (1985) Primary structure of a B1 hordein gene from barley. Carlsberg Res. Commun. 50, 333–345).

C. Other Cassette Elements.

In addition to encoding the protein of interest, the expression cassette's gene may encode a signal/targeting/transport peptide that allows processing and translocation of the protein, as appropriate. Exemplary signal/targeting/transport sequences, particularly for targeting proteins to intracellular bodies, such as vacuoles, are signal/targeting sequences associated with the monocot maturation-specific genes: glutelins, prolamines, hordeins, gliadins, glutenins, zeins, albumin, globulin, ADP glucosepyrophosphorylase, starch synthase, branching enzyme, Em, and lea.

Another exemplary class of signal/targeting/transport sequences are sequences effective to promote secretion of heterologous protein from aleurone cells during seed germination, including the signal sequences associated with α-amylase, protease, carboxypeptidase, endoprotease, ribonuclease, DNase/RNase, (1–3)-alpha-glucanase, (1–3) (1–4) alpha-glucanase, esterase, acid phosphatase, pentosamine, endoxylanase, alpha-xylopyranosidase, arabinofuranosidase, alpha-glucosidase, (1–6) alpha-glucanase, peroxidase, and lysophospholipase.

As above, the heterologous gene-expression cassette may be constructed according to standard recombinant construction methods such as outlined in U.S. Pat. Nos. 5,889,189 and 5,888,789 noted above.

D. Set of Expression Cassettes.

The selectable-marker expression-cassette and heterologous gene expression cassette together form a set of expression cassettes useful in cotransforming monocot plants or plant cells, in accordance with the invention, and as detailed below. This set may include two or more heterologous-gene expression cassettes, each constructed for expression of a different heterologous gene, for producing transformants that produce a panel, e.g., four or more, different heterologous proteins.

Alternatively, the selectable marker cassette and one or heterologous-gene expression cassettes may be constructed as a single expression unit containing, for example, the various expression cassettes arranged in tandem.

IV. Plant Transformation Vector Containing an Expression Cassette

The selectable-marker and heterologous-gene expression cassettes described above may be placed in a suitable expression vector designed for operation in plants. Suitable vectors are described in, for example, above-noted U.S. Pat. Nos. 5,888,789 and 5,889,189.

Expression-cassette vectors for use in the present invention include the selectable-marker expression cassette, together with companion sequences upstream and downstream from the expression cassette. The companion sequences will be of plasmid or viral origin and provide necessary characteristics to the vector to permit the vectors to move DNA from bacteria to the desired plant host. One exemplary vector is the pAPI76 vector constructed as described in Example 1A and illustrated in FIG. 1. The selectable-marker expression cassette therein includes the Gns9 promoter, an HPH coding sequence, and the RAmy1A terminator, and has the sequence identified as SEQ ID NO:2.

Figure 1B:
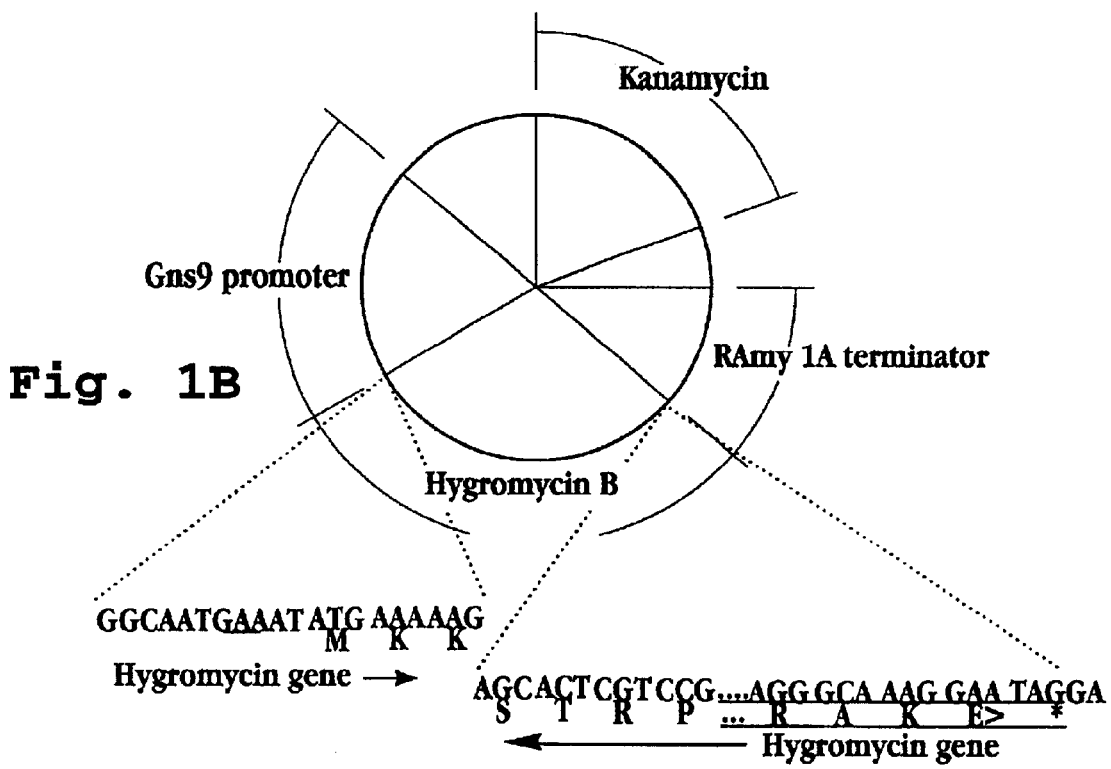
FIG. 1B shows a pAPI-146 vector like pAPI-76, constructed in accordance with another embodiment of the invention.

Another exemplary vector, designated pAPI-146, is illustrated in FIG. 1B. The construction of this selectable-marker expression cassette vector is described in Example 1B.

Both of the two vectors, and analogous vectors containing a heterologous-gene expression vector, are designed for transformation by gold-particle injection, or other direct introduction.

Figure 3A:
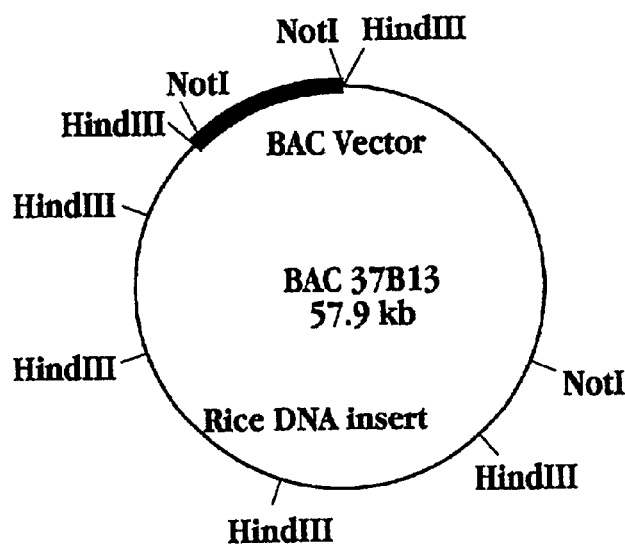
FIGS. 3A and 3B show high molecular weight (>50 kb) plasmid constructs for transformation into callus cells.

Alternatively, the transformation vector containing one or both of the selectable marker expression cassette and the heterologous gene expression cassette may be an Agrobacterium vector, such as the vector shown in FIG. 3A and described in Example 3A. This vector is exemplary of Agrobacterium vectors that can be used to transform plants via Agrobacterium infection.

In addition to the selectable marker cassette and vector, the present invention also contemplates a set of expression vectors containing the selectable-marker cassette and one or more vectors containing heterologous-gene cassettes.

V. Improved Plant Transformation Selection/Regeneration Method Utilizing the Regulated Selectable Marker Expression Cassette The plants used in the process of the present invention are derived from monocots, particularly the members of the taxonomic family known as the Gramineae, This family includes all members of the grass family of which the edible varieties are known as cereals. The cereals include a wide variety of species such as wheat (*Triticum sps.*), rice (*Oryza sps.*) barley (*Hordeum sps.*) oats, (*Avena sps.*) rye (*Secale sps.*), corn (*Zea sps.*) and millet (*Pennisettum sps.*), and sorghum. In the present invention, preferred family members are rice and barley.

A. Transformation

Callus cells derived from the members of the above-described plant family are co-transformed with the selectable marker vector and at least one heterologous protein expression vector containing the heterologous genes of interest, using a variety of standard techniques (e.g., electroporation, Agrobacterium, protoplast fusion, or microparticle bombardment). In the present invention, particle bombardment is the preferred transformation procedure. The heterologous protein expression vector includes a transcription regulatory region (promoter) whose transcription is upregulated in a selected tissue or plant developmental state, and/or by the presence of absence of a small molecule, such as the reduction or depletion of sugar, e.g., sucrose, in culture medium, or in plant tissues, e.g., germinating seeds.

In addition to the expression genes described above, expression cassettes constructed according to the present invention may contain sequences suitable for permitting integration of the coding sequences into the plant genome. These might include transposon sequences, and the like, for homologous recombination, as well as Ti sequences which permit random insertion of a heterologous expression cassette into a plant genome. For Agrobacterium transformations, vectors containing chimeric genes of the present invention may be modified to include T DNA sequences for Agrobacterium-mediated transfer to plant chromosomes. Further, the vectors of the invention may comprise a disarmed plant tumor inducing plasmid of *Agrobacterium tumefaciens*.

Methods for transforming monocot plants or plants cells are known in the literature, as represented by the following references: Li LC, Qu RD, Dekochko A, Fauquet C, Beachy RN (1993) An Improved Rice Transformation System Using the Biolistic Method. Plant Cell Reports 12:250–255; Hiei Y, Ohta S, Komari T, Kumashiro T (1994) Efficient Transformation of Rice (Oryza Sativa L) Mediated By Agrobacterium and Sequence Analysis of the Boundaries of the T-DNA. Plant Journal 6:271–282; Komari T, Hiei Y, Saito Y, Murai N, Kumashiro T (1996) Vectors carrying two separate T-DNAs for co-transformation of higher plants mediated by *Agrobacterium tumefaciens* and segregation of transformants free from selection markers. The Plant Journal 10:165–174; Armstrong C L (1999) The first decade of maize transformation: A review and future perspective. Maydica 44:101–109; Barro F, Rooke L, Bekes F, Gras P, Tatham A S, Fido R, Lazzeri P A, Shewry P R, Barcelo P (1997); Transformation of wheat with high molecular weight subunit genes results in improved functional properties. Nature Biotechnology 15:1295–1299; Battraw M, Hall T C (1991) Stable Transformation of Sorghum-Bicolor Protoplasts With Chimeric Neomycin Phosphotransferase-li and Beta-Glucuronidase Genes. Theoretical and Applied Genetics 82:161–168; Brettschneider R, Becker D, Lorz H (1997) Efficient transformation of scutellar tissue of immature maize embryos. Theoretical and Applied Genetics 94:737–748; Cheng M, Fry J E, Pang S Z, Zhou H P, Hironaka C M, Duncan D R, Conner T W, Wan Y C (1997) Genetic transformation of wheat mediated by *Agrobacterium tumefaciens*. Plant Physiology 115:971–980; Fleming G H, Kramer C M, Le T, Shillito R D (1995) Effect of Dna Fragment Size On Transformation Frequencies in Tobacco (*Nicotiana Tabacum*) and Maize (*Zea Mays*). Plant Science 110:187–192; Frame BR, Drayton P R, Bagnall S V, Lewnau C J, Bullock W P, Wilson H M, Dunwell J M, Thompson J A, Wang K (1994) Production of Fertile Transgenic Maize Plants By Silicon Carbide Whisker-Mediated Transformation. Plant Journal 6:941–948; Hagio T, Blowers A D, Earle E D (1991) Stable Transformation of Sorghum Cell Cultures After Bombardment With Dna-Coated Microprojectiles. Plant Cell Reports 10:260–264; Hamilton D A, Roy M, Rueda J, Sindhu R K, Sanford J, Mascarenhas J P (1992) Dissection of a Pollen-Specific Promoter From Maize By Transient Transformation Assays. Plant Molecular Biology 18:211–218; He D G, Mouradov A, Yang Y M, Mouradova E, Scott K J (1994) Transformation of Wheat (Triticum Aestivum L) Through Electroporation of Protoplasts. Plant Cell Reports 14:192–196, Iser M, Fettig S, Scheyhing F, Viertel K, Hess D (1999) Genotype-dependent stable genetic transformation in German spring wheat varieties selected for high regeneration potential. Journal of Plant Physiology 154:509–516; Ishida Y, Saito H, Ohta S, Hiei Y, Komari T, Kumashiro T (1996) High Efficiency Transformation of Maize (*Zea Mays* L) Mediated By *Agrobacterium Tumefaciens*. Nature Biotechnology 14:745–750; Ortiz J P A, Reggiardo M I, Ravizzini R A, Altabe S G, Cervigni G D L, Spitteler M A, Morata M M, Elias F E, Vallejos R H (1996) Hygromycin Resistance As an Efficient Selectable Marker For Wheat Stable Transformation. Plant Cell Reports 15:877–881; Pareddy D, Petolino J, Skokut T, Hopkins N, Miller M, Welter M, Smith K, Clayton D, Pescitelli S, Gould A (1997) Maize transformation via helium blasting. Maydica 42:143–154; Pukhalskii V A, Smirnov S P, Korostyleva T V, Bilinskaya E N, Eliseeva A A (1996) Genetic transformation of wheat (*Triticum aestivum L.*) by *Agrobacterium tumefaciens*. Genetika 32:1596–1600; Ritala A, Mannonen L, Aspegren K, Salmenkalliomarttila M, Kurten U, Hannus R, Lozano J M, Teeri T H, Kauppinen V (1993) Stable Transformation of Barley Tissue Culture By Particle Bombardment. Plant Cell Reports 12:435–440; Takumi S, Shimada T (1997) Variation in transformation frequencies among six common wheat cultivars through particle bombardment of scutellar tissues. Genes & Genetic Systems 72:63–69; Torbert K A, Rines H W, Somers D A (1995) Use of Paromomycin As a Selective Agent For Oat Transformation. Plant Cell Reports 14:635–640; Torbert K A, Rines H W, Somers D A (1998) Transformation of oat using mature embryo-derived tissue cultures. Crop Science 38:226–231; Walters D A, Vetsch C S, Potts D E, Lundquist R C (1992) Transformation and Inheritance of a Hygromycin Phosphotransferase Gene in Maize Plants. Plant Molecular Biology 18:189–200; Witrzens B, Brettell R I S, Murray F R, McElroy D, Li Z Y, Dennis E S (1998) Comparison of three selectable marker genes for transformation of wheat by microprojectile bombardment. Australian Journal of Plant Physiology 25:39–44; and Zhang J, Tiwari V K, Golds T J, Blackhall N W, Cocking E C, Mulligan B J, Power J B, Davey M R (1995) Parameters Influencing Transient and Stable Transformation of Barley (Hordeum Vulgare L) Protoplasts (Vol 41, Pg 125, 1995). Plant Cell Tissue and Organ Culture 43:83–83.

B. Selection/Regeneration

The improved selection/regeneration method, described in Example 2, takes advantage of the unique properties of the regulated promoter which drives expression of the selectable marker gene. The regulated promoter, as described above, strongly expresses the selectable marker gene product (e.g., HPH) in callus cells. Therefore, callus cells transformed with and expressing the selectable marker gene are able to grow in the presence of the selection agent (e.g., hygromycin B). After the transformed calli are identified and are isolated from the non-transformed calli, the transformed calli are then regenerated into plantlets in the absence of the selection agent.

To verify the conclusion that the selectable marker gene is expressed in callus, but not differentiated plant tissue, the GUS gene was placed under the control of the Gns-9 promoter and used to transform rice plant material. Expression of the GUS gene, as evidenced by a blue color, was observed in callus tissue, but no color was seen in regenerating plants or in seeds during germination. In a second test, it was verified that transformed callus tissue containing the hygromycin phosphotransferase selectable marker gene was readily selected in the presence of hygromycin B. Germinating seeds from the transformed plants, on the other hand, lacked the ability to germinate in a germination medium also containing hygromycin B, demonstrating that the seeds were expressing little if any of the selectable marker enzyme.

Specifically, it was observed that all plants in hygromycin B containing media either die or turn yellow. Two stunted plants were developed with brown roots. These plants were eventually dead due to the poor rooting system. Healthy plants were developed from calli in media without hygromycin B.

To test if transgenic seeds can germinate on hygromycin B containing media, 10 transgenic seeds were placed on hygromycin B containing media and 10 seeds were placed on to the same media but without hygromycin B. Seeds on hygromycin B-free media germinate and grow rapidly while the 10 transgenic seeds were not able to germinate and develop healthy plants. The reason for not being able to develop healthy plants from these transgenic calli and seeds is due to the fact that the 940 bp Gns 9 promoter was not active to express its downstream gene-hygromycin gene, in root, leaves and seeds even though these seeds and calli were from transgenic callus which were selected based on their resistance to the same concentration of hygromycin B in the media.

The novel regeneration step performed in the absence of selective pressure greatly enhances the efficiency of recovery of the transgenic plants. While not being bound by theory, the increased efficiency of recovery may be in part attributable to the absence of the selective agent, as well as the down-regulation of the selectable marker promoter in the emerging plantlets. The decreased expression of the selectable marker gene product as the calli regenerate into plantlets relieves the metabolic stress placed on the regenerating plants during this critical phase of plant transformation. In contrast, constitutive promoters remain active during this regeneration phase, placing an additional metabolic load on the plantlet and a lower efficiency of recovery.

As well as enhancing the efficiency of recovery of the emerging plantlets, the improved selection/regeneration method has additional benefits, such as substantial cost savings realized in the reduced amount of selection agent required.

VI. Simultaneous Introduction of Multiple Heterologous Genes into Callus Cells

The high efficiency of recovery realized by utilization of the novel selectable marker construct together with the improved selection/regeneration method described above has been found to significantly increase the probability of low-frequency transformation events, such as the introduction of multiple genes or very large DNA molecules into callus cells in a single transformation event.

Example 3 describes the successful integration of nine heterologous genes, including the selectable marker gene, introduced by simultaneous transformation with a total of nine plasmids (including the selectable marker plasmid) using the improved selection/regeneration method in conjunction with regulated promoter-selectable marker construct described above, with the results are shown in FIGS. 2A–2I. In these studies, five plants (callus cells) were transformed simultaneously with heterologous-gene expression cassettes (vectors) containing, as heterologous genes, BPN' (2A), AAT (2B), HepC (2C), HbsAg (2D), GUS (3E), GFP (2F), Hph (2G), Bar (2H), and luc (2I).

Details of the analysis of transformation is given in Example 3. Briefly, PCR analysis showed that all regenerated plants transformed, selected, and regenerated as described above carried the hph gene. Five representative transgenic plants were then subjected to Southern analysis to determine the frequency at which all nine genes co-integrated into the rice genome (FIG. 2). Integration of the genes takes place in single to multiple copies. Two of the five transgenic plants (10p-8 and 10p-34) contained DNA from all nine plasmids. The remaining plants carried DNA from seven (10p-28 and 10p-64) or eight (10p-2) of the nine co-transformed genes.

Figure 4A:
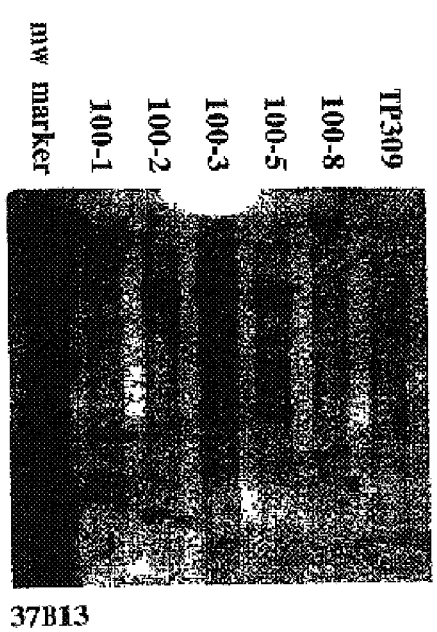
FIGS. 4A and 4B are Southern blots showing the stable integration of DNA from the high molecular weight plasmids of FIG. 3A, introduced into transgenic plants using the improved selection/regeneration method in conjunction with regulated promoter-selectable marker construct of the present invention.
Figure 4B:
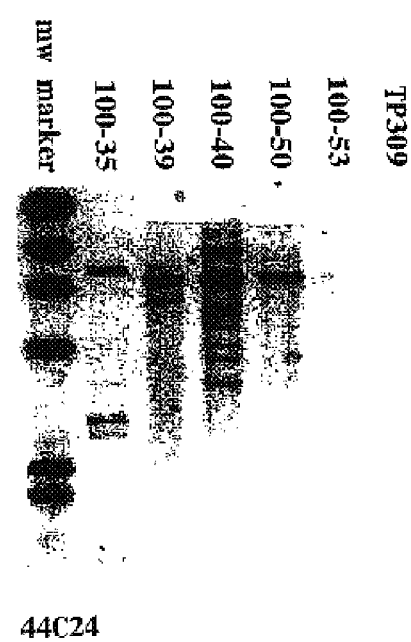

Example 4 describes the successful transformation and integration of 50 kb high molecular weight plasmids into callus cells using the improved selection/regeneration method in conjunction with regulated promoter-selectable marker construct. Exemplary results are shown in FIGS. 4A and 4B.

Both the multiple plasmid transformation and high molecular weight plasmid transformation methods allow the simultaneous introduction of multiple genes into the transgenic plant. These types of transformation schemes allow, for example, metabolic engineering in monocot plants, in which the expression of numerous genes in a pathway is up-regulated and the flux of the pathway is maximized by introduction of additional homologous and/or heterologous metabolic genes.

Another application of monocot transformation with high molecular weight plasmids is for the complementation test in gene cloning by phenotype. For example, to clone the Xa21 gene, Song et al. (1995; Science 270:1804–6) identified several cosmid clones in the range of 35 to 50 kb. Limitations on the transformation technology at that time necessitated the subcloning of these cosmids into smaller plasmids before transformation was conducted, which is rendered unnecessary by the improvement described herein.

The simultaneous transformation of monocot plant cells with multiple heterologous gene-carry plasmids, or high molecular weight plasmids, by the method of the present invention thus represents a significant technological improvement in the field of monocot plant gene expression.

The following examples are provided by way of illustration only and not by way of limitation. Those of skill will readily recognize a variety of non-critical parameters which could be changed or modified to yield essentially similar results.

General Methods

Generally, the nomenclature and laboratory procedures with respect to standard recombinant DNA technology can be found in Sambrook, et al., *MOLECULAR CLONING: A LABORATORY MANUAL*, Cold Spring Harbor Laboratory, Cold Spring Harbor, N.Y. (1989) and in S. B. Gelvin and R. A. Schilperoot, *PLANT MOLECULAR BIOLOGY* (1988). Other general references are provided throughout this document. The procedures therein are known in the art and are provided for the convenience of the reader.

EXAMPLES 1A–1C

Selectable Marker Vector Construction

A. pAPI-76 Vector

An exemplary selectable marker vector was constructed in three steps. First, a DNA fragment was amplified from the rice alpha-amylase gene, RAmy1A, (Huang N. et al. (1990) Plant Molecular Biology 14:655–668), using the primers 1AR1: 5' AAC AAT ACT GGA ATT CGA GAA GTA AAA AG 3' (SEQ ID NO:5) and 1ASma: 5' CTA CGC AAC CCG GGA GAA AAT C 3' (SEQ ID NO:6). The amplified fragment, containing 297 bp of the RAmy1A terminator, was cloned into the SmaI/EcoRI restriction sites of pBluscript KS+, resulting in plasmid p1AT. Second, a BamHI DNA fragment from plasmid pGL2 (Shimamoto et al. (1989)

Nature 338:274–276) encoding hygromycin phosphotransferase (HPH) was cloned into the BamHI site of p1AT, resulting in plasmid pAPI74. The pGL2 BamH1 fragment encodes the full-length HPH polypeptide sequence minus four C-terminal amino acids. Third, a SacI/XbaI fragment was amplified from rice beta-glucanase gene Gns9 using the primers gnsF, 5' GAC TTA ACT TTA GTC ATA TTT AG 3' (SEQ ID NO:7) and GnsR 5' TTC GCT CTT GCT GCT GCT CACT 3' (SEQ ID NO:8) and was inserted into the SacI/XbaI sites of pAPI74 to form pAPI76. The sequence of all fragments was confirmed by DNA sequencing.

Figure 1C:
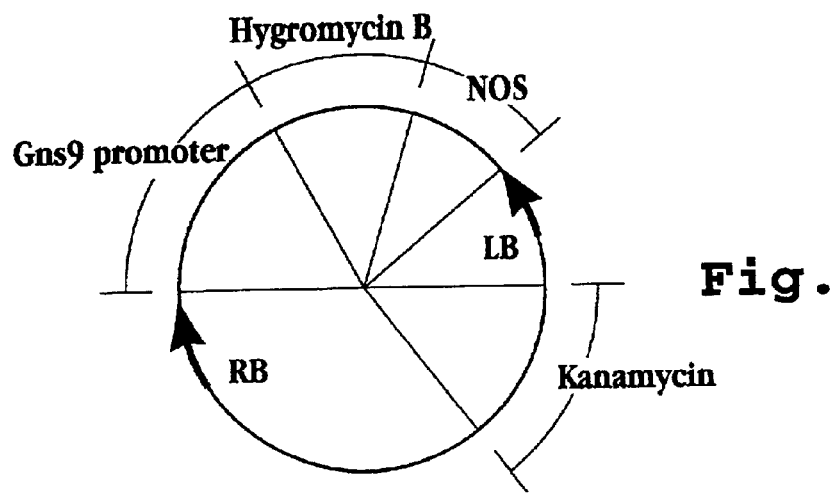
FIG. 1C shows a pAPI-353 Agrobacterium single-cassette vector constructed in accordance with yet another embodiment of the invention.

As shown in FIG. 1, the 5206 bp selectable marker vector described above contains a chimeric selectable marker gene comprising the Gns9 promoter, an HPH coding sequence which lacks the four C-terminal codons and stop codon of the hph gene, and an RAmy1A terminator. Since there is no stop codon in the BamHI HPH-encoding fragment, the translation reads through the HPH C-terminus into the RAmy1A terminator, generating a fusion protein with an additional C-terminal 14 amino acids (indicated in the inset of FIG. 1), most of which are hydrophilic.

B. Further Improvement to pAPI-76 Vector.

First, the extra ATG near the translational start codon was removed by site-directed mutagenesis (SDM), and for cloning purpose, a BamHI site was changed to BgIII sites at the same time. Two site specific mutagenesis primers are synthesized:

```
API Primer #110-Hph-SDM1
            BamHI (pAPI 76)
       GGATCC     T
GCAGTCTAGAACTAGTAGATCTCGGGGGGCAACGAAATATGAAAAAGCC
(SEQ ID NO: 9)

BgIII
API Primer #109   Hph-SDM2
GGCTTTTTCATATTTCGTTGCCCCCCGAGATCTACTAGTTCTAGACTGC
(SEQ ID NO: 10)
```

The mutagenesis was done by using PCR and Quick Change Kit from Stratgene, Calif. The resulting plasmid is called pAPI76(SDM). To repair the C-terminus of pAPI76 (SDM), the following two primers were synthesized in order to generate a PCR fragment:

```
    API Primer #111-Hph-Rev
           E K A R
T AAT GGA TCC TCA TTC CTA TTC CTT TGC CCT CGG ACG AGT GCT GGG G
(SEQ ID NO: 11)
   BamHI stop  stop API Primer #114-Hph-fwd
    ATCGCCGCGGCTCCGGGCGTATATGC
(SEQ ID NO: 12)
       SacII
```

The PCR fragment that was generated with the two primers, using pAPI76 as a template, was digested with SacII and BamHI and inserted into pAPI76(SDM) which as been cut with SacII/BamHI. The resulting plasmid is called pAPI106. DNA sequencing confirmed the correct site directed mutagenesis.

Both pAPI76 and pAPI106 are in plasmid backbone containing Amp resistance gene. To replace the amp gene with a kan gene, two steps were taken.

Replacement of â-Lactamase (ampicillin res.) in pUC19 with aminoglycoside phosphotransferase (kananmycin res.) from pCR2.1:

The â-lactamase gene was cut from pUC19 using SspI and DraI creating four DNA fragments of 1748, 692, 227, and 19 bp with 1748 bp fragment being the vector band to be excised. These enzymes left blunt ends at the restriction sites. The kanamycin resistance gene was amplified by the PCR from pCR2.1 with PfU polymerase thus leaving blunt ends on the PCR product for cloning into pUC19 (the 1748 fragment).

Primer-1 (KANF1) begins 146 nt upstream of the ATG for the kan$^r$ gene and primer-2 (KANR1) ends 19 nt downstream of the stop codon for the same gene.

```
             SspI half site
Primer-1 = KanF1 5'-ATTGCAAGCGAACCGGAATTGCCAG -3'
(SEQ ID NO: 13)

DraI half site
Primer-2 = KanR1 5'-AAACTCTTCCTTTTTCAATTCAG -3'
(SEQ ID NO: 14).
```

Nucleotide additions were made to the PCR primers to preserve the restriction sites used for cloning. The ligation was then transformed to *E coli*, which was placed on kanamycin-containing media. Plasmids isolated from Kan resistant colonies were analyzed for the replacement of Amp gene with Kan gene. The resulting plasmid was called pUC19Kan.

To place the Gns9-hph-1A cassette into pUC19Kan, pAPI106 was double-digested with HindIII and SacI. The HindIII/SacI fragment was then isolated and inserted into pUC19Kan which was precut with HindIII and SacI. The final plasmid is called pAPI146.

C. Agrobacterium Vector.

Plasmid, pJH2600, kindly provided by Dr. Diter von Wettstein, Washington State University, was used to generate a new selectable marker plasmid for cereal transformation with Agrobacterium. The vector size is about 14.3 kb. A SacI/EcoRI fragment is isolated from pAPI146 and inserted into pJH2600 cut with the same enzyme. The resulting plasmid is called pAP1352. Then the EcoR1 fragment is cut out from pAPI146 and put into pAP1352, which was digested with EcoRI as well. Plasmid with correct orientation of EcoRI fragment, is identified by DNA sequencing through the junction region of the hph gene. The plasmid is named pAPI353.

EXAMPLE 2

Rice Transformation, Selection, And Plant Regeneration

The basic procedure of microprojectile-mediated rice transformation (Sivamani E., et al. (1996) Plant Cell Rep.

15:322–327; Zhang S. et al. (1996) Plant Cell Rep. 15:465–469) was modified as follows. About 200 TP309 rice seeds were dehulled, sterilized in 50% commercial bleach for 25 min and washed with sterile water three times for 5 min each. Sterilized seeds were placed on seven plates containing N6 media (Sigma Chemical Co.; St. Louis, Mo.) to induce calli for 10 days. The primary callus was dissected and placed on fresh N6 media for three weeks. The secondary callus was separated from the primary callus and placed on N6 media to generate a tertiary callus. The tertiary callus was used for bombardment and sub-cultured 4–5 times every two weeks.

Calli 1 to 4 mm in diameter were selected and placed as a 4 cm circle on N6 media with 0.3 M mannitol and 0.3 M sorbitol for 5–24 hrs before bombardment. Biolistic bombardment was carried out with the Biolistic PDC-1000/He system (BIORAD, Richmond, Calif.). The procedure required 1.5 mg of gold particles (60 ug/ul) coated with 2.5 ug pAPI76 DNA. DNA-coated gold particles were bombarded into the rice callus with a helium pressure of 1100 psi. After bombardment, the calli were allowed to recover on the same plate for 48 hrs and then transferred to NB media with 20 mg/l hygromycin B. The bombarded calli were incubated on the selection media in the dark at 26° C. for 45 days. Transformants, which appeared opaque white, compact, and were readily distinguishable from non-transformants which were yellow-brown, soft, and watery, were selected and transferred to pre-regeneration media (PRH) consisting of N6 (without 2,4-D), 5 mg/l ABA, 2 mg/l BAP, 1 mg/l NAA and 20 mg/l hygromycin B for 9 to 12 days. The transformants were then transferred to the regeneration media (RN) consisting of N6 (without 2,4-D), 3 mg 1 L BAP, 0.5 mg/L NM and without hygromycin B, and cultured under continued lighting conditions for about two weeks. When the regenerated plants were 1 to 3 cm high, the plantlets were transferred to the rooting media which was half the strength of the MS media containing 0.05 mg/l NM. In two weeks, the plantlets in the rooting media developed roots and its shoots grew over 10 cm. The plants were then transferred to a 2.5 in. pot containing 50% commercial soil, Sunshine #1 (Sun Gro Horticulture Inc, WA) and 50% natural soil. The pots were placed within a transparent plastic container to maintain 100% humidity. The plants were cultured under lighting conditions for 1 week. The transparent plastic cover was then opened little by little over one day to gradually reduce humidity, after which the plastic cover was removed completely. Water and fertilizers were added as necessary. When the plants grew to approximately 5 in. tall, they were transferred to a greenhouse to grow to maturity.

Table 1 shows the results of experiments performed to determine the correlation between integration of the selectable marker gene and integration of heterologous "target" genes carried on vectors co-transformed with the selectable marker vector. PCR analysis for stable integration of the hph selectable marker gene showed 100% of the regenerated rice plants transformed and selected as described above contained the hph gene. Various target genes (such as GUS) carried on vectors co-transformed together with the selectable marker vector also integrated with very high efficiency as confirmed by PCR analysis (Table 2) and by Southern blot analysis. Overall, 97% of the regenerated plants co-transformed with the selectable marker vector and a target vector carried the target gene in addition to the selectable marker gene.

TABLE 1

| Target vector | Selectable marker vector | Selectable marker gene | | Target gene | |
|---|---|---|---|---|---|
| | | PCR positive | PCR negative | PCR positive | PCR negative |
| pAPI65 | pAPI76 | 33 | 0 | 33 | 0 |
| pAPI72 | pAPI76 | 27 | 0 | 27 | 0 |
| pAPI96 | pAPI76 | 30 | 0 | 30 | 0 |
| pAPI85 | pAPI76 | 26 | 0 | 22 | 4 |
| pAPI98 | pAPI76 | 13 | 0 | 13 | 0 |
| pAPI90 | pAPI76 | 13 | 0 | 13 | 0 |
| pAPI64 | pAPI76 | 13 | 0 | 13 | 0 |
| pAPI78 | pAPI76 | 28 | 0 | 26 | 2 |
| Totals | | 183 | 0 | 177 | 6 |

EXAMPLE 3

Transformation of Callus Cells With Multiple Plasmids

To transform the rice calli with multiple plasmids, nine different plant transformation vectors prepared essentially as described above were selected. Eight of the plasmids contained heterologous genes, and the ninth expressed the chimeric selectable marker gene constructed as detailed above. The nine plasmids were mixed in 1:1:1:1:1:1:1:1:1 molar ratio (i.e., a ratio of heterologous vector DNA to selectable marker vector DNA of 8:1). A total of 40 µg of the vector mixture was used to coat 48 mg gold particles and used to bombard three plates.

PCR analysis showed that all regenerated plants transformed, selected, and regenerated as described above carried the hph gene. Five representative transgenic plants were then subjected to Southern analysis to determine the frequency at which all nine genes co-integrated into the rice genome (FIG. 2). Integration of the genes takes place in single to multiple copies. Two of the five transgenic plants (10 p-8 and 10 p-34) contained DNA from all nine plasmids. The remaining plants carried DNA from seven (10p-28 and 10p-64) or eight (10 p-2) of the nine co-transformed genes.

D. Rice Transformation With High Molecular Weight Plasmids

High molecular weight plasmids were from a bacterial artificial chromosome (BAC) library (Yang D C, et al. (1997) Theor. Appl. Genet. 95:1147–1154). The BAC DNA and the pAPI76 selectable marker vector were mixed in a 1:1 molar ratio before coating the gold particles. Approximately 40 µg of the mixed DNA was used to coat 48 mg gold particles to bombard of three plates. Bombardment, selection, and plant regeneration were as described above.

Figure 3B:
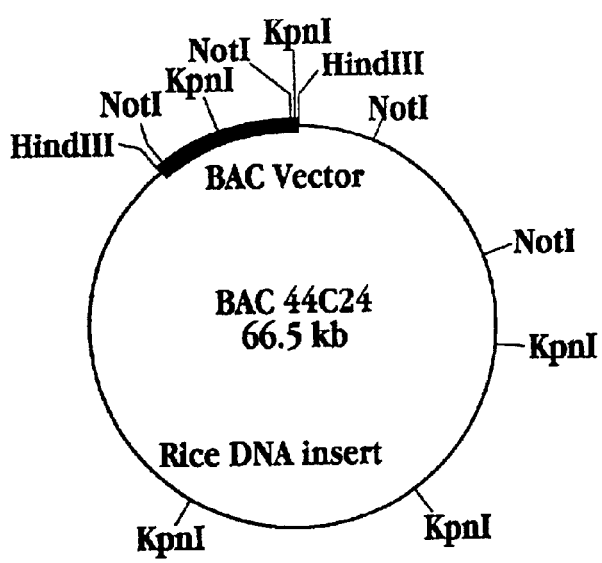
Figure 2A:
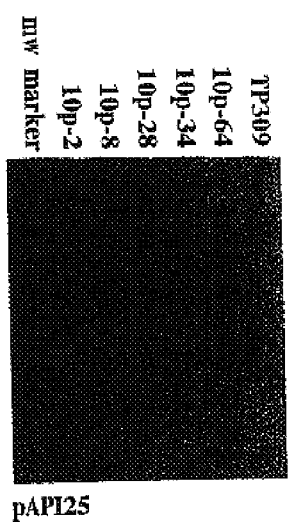
FIGS. 2A–2I are Southern blots showing the stable integration of nine heterologous genes (A-I), including the selectable marker gene, in transgenic plants by simultaneous transformation with nine plasmids using the improved selection/regeneration method of the invention in conjunction with regulated promoter-selectable marker construct of the present invention.
Figure 2B:
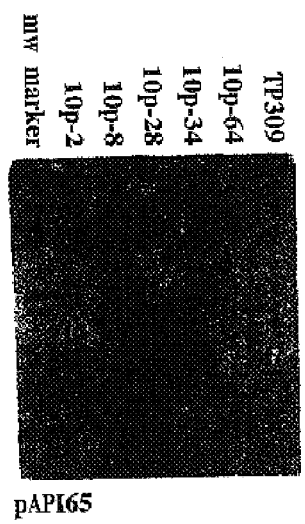
Figure 2C:
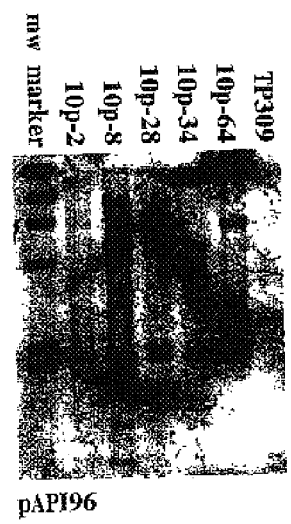
Figure 2D:
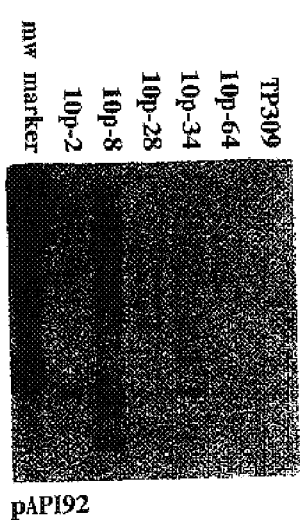
Figure 2E:
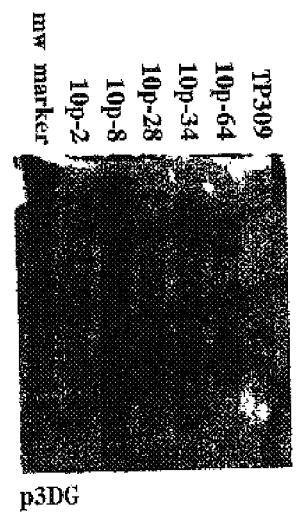
Figure 2F:
Figure 2G:
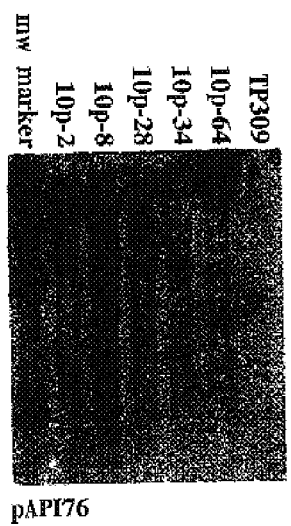
Figure 2H:
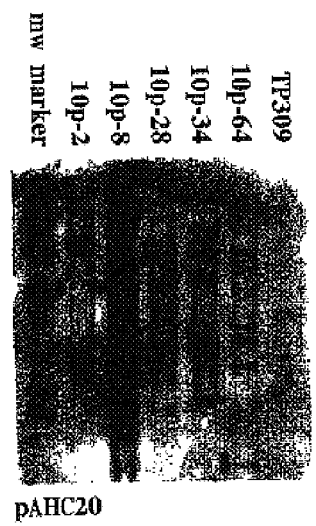
Figure 2I:

Restriction mapping indicated that the molecular weight of the two BAC clones (FIG. 3A) were over 50 kb. After transformation, seventy-seven plants were obtained. PCR analysis with hph and chloramphenicol genes showed that most of the plants carried both genes. DNA from 5 representative transgenic plants were analyzed by Southern blot (FIG. 3B). Since the inserts of BAC clones were from a rice genome (Yang et al., supra), it was difficult to distinguish transformed DNA and native DNA, therefore the vector fragment of the BAC clone was used as probe. It is assumed that if the vector DNA can integrate into rice genome, any portion of BAC DNA on the same plasmid has an equal chance to integrate into the rice genome.

EXAMPLE 4

A further exemplary selectable marker vector was constructed with the BAR (phosphinothricin acetyltransferase)

gene expressed under the control of the Gns9 promoter having the sequence presented as SEQ ID NO:1. The sequence of the 4704 bp construct (API 291) is shown in FIGS. 5A–G (SEQ ID NO:4), and represents a chimeric selectable marker gene comprising the Gns9 promoter, the coding sequence for the phosphinothricin acetyltransferase gene, and a NOS terminator.

Rice callus was transformed with this construct, selected and regenerated using the methods detailed in Example 2.

Wheat immature embryos were transformed via Particle bombardment with this construct and with a selectable marker vector comprising the hygromycin phosphotransferase coding sequence, selected and regenerated using the methods detailed below.

1.1.1 Grow Bobwhite Wheat in a Growth Chamber
- 15 plants per cycle
- Day/night is 16 hr/8 hr, 18° C./16° C., light is 800 μE,
- Humidity is 80%.
- 6-inch pot, 5 seeds/pot 1.1.2 Harvest Spikes and Husk Caryopses
- Harvest spikes 12–14 days after anthesis. The immature embryos should be young and slightly starchy and 0.8 to 1.5 mm in size.
- Remove caryopses from spikes, place it in a 50 ml centrifuge tube, cap it.

1.1.3 Sterilization of Bobwhite Wheat Immature Embryos
- Add 5 ml of 70% ethanol, shake for 1–2 minutes
- Discard the Ethanol
- Add 30 ml of 20% commercial bleach, shake for 45 minutes on a shaker.
- Rinse with sterile dd $H_2O$.
- Wash 3 times with sterile dd $H_2O$, 5 minutes each time.

1.1.4 Isolation of Immature Embryos
- Place the sterilized caryopses in a petri dish.
- Use scalpel and forceps to dissect it.
- Place embryo on wheat callus induction medium (WCI) with scutellum-side up at 26° C. in the dark for 3 days. 80–100 embryos/plate 1.2 Plasmid DNA
- pAPI146 (Gns9-hph) or pAPI291 (Gns9-Bar) as selectable marker
- API genes of interest as target DNA which will be co-bombarded with selectable marker.

2. Method 2.1 Pretreatment of Immature embryos (IEs)
- Pick small and compact precultured IEs (cells actively dividing but no callus formation)
- place on WCI with Sorbitol (0.2M) and Mannitol (0.2M)
- Incubate at 26° C. in the dark for 5–24 hour.

2.2 Particle Coating
- 4.2 μg of DNA mixture (GOI: SM=2:1, 1:1:1, I:I:I:I, orI:I:I:I:1)
- Add 100 μl of gold solution (60 mg/ml), mix well
- Add 40 μl of 0.1 M spermidine, mix well
- Add 100 μl of 2.5 M $CaCl_2$, mix well
- Incubate at room temperature for 10 minutes
- Centrifuge for 5 seconds at full speed, and discard the supernatant
- Add 600 μl of cold ethanol (100%), mix well
- Centrifuge for 5 seconds at full speed, and discard the supernatant
- Add 300 μl of 100% ethanol
- Set it on ice before loading onto microcarrier disks 2.3 Bombardment 2.3.1 Loading DNA-Gold onto Microcarrier Disk
- Mix DNA-Gold solution very well
- Pipette 10 μp1 of DNA-Gold and quickly spread onto the center (1 cm) of the disk as even as possible.
- Let the DNA-Gold dry
- Load tow more times on the same disk, allow it dry between loadings.
- It is ready to bombardment after the DNA-Gold dry.

2.3.2 Bombardment
- Vacuum-27 in Hg
- Repture disk-1100 psi
- Target position-8 cm from stopping screen (third shelf)
- One shots per plate 3. Selection
- After bombardment, remain the IEs on the same plate and incubate at 26° C. in the dark for 1–2 days.
- Transfer the IEs (30 IEs per plate) onto WCIH50 (WCI containing 50 mg/L hygromycin B) or WCIB5 (WCI containing 5 mg/L Bialaphos) base on which selectable marker used.
- Incubate at 26° C. in the dark for 30 days,
- Transfer fast growth callus onto fresh selection medium for another 30 days.

4. Regeneration
- After 60 days selection, transfer survive callus onto HFG regeneration medium (with out selection reagent), 7 calli per plate.
- Incubate under continuous light at 28° C. until the callus develop shoots up to 1 cm.
- Transfer green shoots into Magenta Box with Rooting Medium (RM), 4 plantlets per box.
- Incubate at 28° C. in the light until the shoot develops root system.
- Transfer plantlets into 4-inch pot containing potting soil
- Pace the transgenic plant in a growth chamber until maturity

It is claimed:

1. A method of transforming rice plants with one or more heterologous nucleic acid coding sequences capable of producing heterologous proteins in the rice, under selected induction conditions, comprising cotransforming rice callus cells with a set of two or more expression cassettes, said set comprising:
   (a) a chimeric selectable marker expression cassette having, operatively linked in sequence in a 5' to 3' direction, (i) a transcriptional regulatory region which expresses in transformed callus cells at a significantly higher level than in seed tissue, and hybridizes under high stringency conditions with the complement of the rice β-glucanase gene (Gns9) promoter identified by SEQ ID NO:1; (ii) a phosphinothricin acetyltransferase-coding sequence and (iii) a 3' untranslated terminator region; and
   (b) at least one heterologous gene expression cassette, having operatively linked in sequence in a 5' to 3' direction, (i) a transcriptional regulatory region that is expressed, induced or inducible in plant seeds, (ii) a first DNA sequence encoding a selected heterologous protein, and (iii) a 3' untranslated terminator region, wherein the transcriptional regulatory region in said heterologous-gene expression cassette is induced during seed maturation or seed germination;
   (i) culturing the callus cells in the presence of a selection agent effective to block growth of callus cells in the absence of expression of the phosphinothricin acetyltransferase-encoding nucleic acid sequence;
   (ii) selecting those callus cells that express the phosphinothricin acetyltransferase enzyme, as evidenced by their growth in the presence of the selection agent; and
   (iii) regenerating the selected callus cells into transgenic plants under non-selection conditions.

2. A rice plant transformed by the method of claim 1.

3. A plant transformation expression cassette for transforming rice plant cells with a chimeric selectable marker gene, said cassette comprising, in a 5' to 3' direction:
   (i) a transcriptional regulatory region comprising a sequence which hybridizes under high stringency conditions with the rice β-glucanase gene promoter identified by SEQ ID NQ:1, and which expresses in callus cells at a significantly higher level than in a selected target tissue,
   (ii) a phosphinothricin acetyltransferase encoding selectable marker coding sequence, and
   (iii) a 3' untranslated terminator region.

4. A plant transformation expression cassette according to claim 3, wherein the transcriptional regulatory region in the selectable marker gene is the Gns9 promoter identified by SEQ ID NO:1 or an operative portion thereof, said portion sufficient to promote expression in transformed callus cells at a significantly higher level than in a selected target tissue.

5. A rice plant produced by regenerating a plant cell transformed with the expression cassette of claim 4.

6. A transgenic rice seed comprising:
a chimeric selectable marker gene including a phosphinothricin acetyltransferase selectable marker coding sequence under the control of a transcriptional regulatory region that is induced in callus tissue at a significantly higher level than in seed tissue and hybridizes under high stringency conditions with the complement of the rice β-glucanase gene (Gns9) promoter identified by SEQ ID NO:1, and
a heterologous protein coding sequence under the control of a transcriptional regulatory region that is induced or inducible during seed maturation or germination.

7. The transgenic rice seed of claim 6, wherein said chimeric selectable marker gene has the sequence identified by SEQ ID NO:4.

8. A plant transformation expression cassette according to claim 4, wherein said chimeric selectable marker gene has the sequence identified by SEQ ID NQ:4.

* * * * *